United States Patent
Li et al.

(10) Patent No.: US 12,152,065 B2
(45) Date of Patent: Nov. 26, 2024

(54) T CELL RECEPTOR FOR IDENTIFYING AFP ANTIGEN

(71) Applicant: XLIFESC, LTD., Guangdong (CN)

(72) Inventors: Yi Li, Guangdong (CN); Jing Hu, Guangdong (CN); Jun Li, Guangdong (CN); Hanli Sun, Guangdong (CN)

(73) Assignee: XLIFESC, LTD., Guangdong (CN)

( * ) Notice: Subject to any disclaimer, the term of this patent is extended or adjusted under 35 U.S.C. 154(b) by 974 days.

(21) Appl. No.: 17/264,649

(22) PCT Filed: Jul. 29, 2019

(86) PCT No.: PCT/CN2019/098245
§ 371 (c)(1),
(2) Date: Jan. 29, 2021

(87) PCT Pub. No.: WO2020/024915
PCT Pub. Date: Feb. 6, 2020

(65) Prior Publication Data
US 2021/0324034 A1    Oct. 21, 2021

(30) Foreign Application Priority Data
Jul. 30, 2018 (CN) .......................... 201810854117.4

(51) Int. Cl.
| | |
|---|---|
| *C07K 14/725* | (2006.01) |
| *A61K 47/62* | (2017.01) |
| *C12N 15/86* | (2006.01) |
| *A61K 38/00* | (2006.01) |

(52) U.S. Cl.
CPC .......... *C07K 14/7051* (2013.01); *A61K 47/62* (2017.08); *C12N 15/86* (2013.01); *A61K 38/00* (2013.01); *C12N 2740/15043* (2013.01)

(58) Field of Classification Search
None
See application file for complete search history.

(56) References Cited

U.S. PATENT DOCUMENTS 11,041,011 B2 *  6/2021  He ..................... C07K 14/7051

FOREIGN PATENT DOCUMENTS

WO    2014/206304 A1    12/2014

OTHER PUBLICATIONS

Sun et al., "Engineered Cytotoxic T lymphocytes with AFP-specific TCR Gene for Adoptive Immunotherapy in Hepatocellular Carcinoma", Tumor Biol., vol. 37, pp. 799-806, Aug. 7, 2015, Cited in International Search Report.
Katoh et al., "Immunogenetic Profiling for Gastric Cancers Identifies Sulfated Glycosaminoglycans as Major and Functional B Cell Antigens in Human Malignancies", Cell Reports, vol. 20, pp. 1073-1087, Aug. 1, 2017, Cited in International Search Report.
Le Nours et al., "Atypical Natural Killer T-cell Receptor Recognition of CD1d-lipid Antigens", Nature Communications, vol. 7, No. 10570, pp. 1-14, Feb. 15, 2016, Cited in International Search Report.
Collins et al., "TCR-MHC docking orientation: natural selection, or thymic selection?", Immunol., Res., vol. 41, pp. 267-294, Aug. 26, 2008, Cited in International Search Report.
Aleksic et al., "Different affinity windows for virus and cancer-specific T-cell receptors—implications for therapeutic strategies" Eur. J. Immunol., vol. 42, pp. 3174-3179, Dec. 31, 2012, Cited in International Search Report.
Butterfield et al., "T Cell Responses to HLA-A*0201-Restricted Peptides Derived from Human a Fetoprotein", J. Immunol., vol. 166, pp. 5300-5308, Dec. 31, 2001, Cited in International Search Report.
International Search Report and Written Opinion, International Patent Application No. PCT/CN2019/098245, Nov. 4, 2019, with English translation of Search Report (17 pages).

* cited by examiner

*Primary Examiner* — Agnieszka Boesen
(74) *Attorney, Agent, or Firm* — HSML P. C.

(57) ABSTRACT

A T cell receptor (TCR) capable of specifically binding to a short peptide FMNKFIYEI derived from an AFP antigen. The antigen short peptide FMNKFIYEI can form a complex with HLA A0201 and be presented together with same to the cell surface. A nucleic acid molecule encoding the TCR, a vector comprising the nucleic acid molecule, and a cell that transduces the TCR.

26 Claims, 11 Drawing Sheets
Specification includes a Sequence Listing.

KQEVTQIPAALSVPEGENLVLNCSFTDSAIYNLQWFRQDPGKGLTSLLLIQSSQR
EQTSGRLNASLDKSSGRSTLYIAASQPGDSATYLCAVNSGGSNYKLTFGKGTLL
TVNPN (SEQ ID NO.1)

Fig. 1A aaacaggaggtgacacagattcctgcagctctgagtgtcccagaaggagaaaacttggttctcaactgcagtttcactgata
gcgctatttacaacctccagtggtttaggcaggaccctgggaaaggtctcacatctctgttgcttattcagtcaagtcagagag
agcaaacaagtggaagacttaatgcctcgctggataaatcatcaggacgtagtactttatacattgcagcttctcagcctggtg
actcagccacctacctctgtgctgtgaatagtggaggtagcaactataaactgacatttggaaaaggaactctcttaaccgtg
aatccaaat (SEQ ID NO.2)

Fig. 1B

KQEVTQIPAALSVPEGENLVLNCSFTDSAIYNLQWFRQDPGKGLTSLLLIQSSQR
EQTSGRLNASLDKSSGRSTLYIAASQPGDSATYLCAVNSGGSNYKLTFGKGTLL
TVNPNIQNPDPAVYQLRDSKSSDKSVCLFTDFDSQTNVSQSKDSDVYITDKTVL
DMRSMDFKSNSAVAWSNKSDFACANAFNNSIIPEDTFFPSPESSCDVKLVEKSF
ETDTNLNFQNLSVIGFRILLLKVAGFNLLMTLRLWSS (SEQ ID NO.3)

Fig. 1C aaacaggaggtgacacagattcctgcagctctgagtgtcccagaaggagaaaacttggttctcaactgcagtttcactgata
gcgctatttacaacctccagtggtttaggcaggaccctgggaaaggtctcacatctctgttgcttattcagtcaagtcagagag
agcaaacaagtggaagacttaatgcctcgctggataaatcatcaggacgtagtactttatacattgcagcttctcagcctggtg
actcagccacctacctctgtgctgtgaatagtggaggtagcaactataaactgacatttggaaaaggaactctcttaaccgtg
aatccaaatAtccagaaccctgaccctgccgtgtaccagctgagagactctaaatccagtgacaagtctgtctgcctattcac
cgattttgattctcaaacaaatgtgtcacaaagtaaggattctgatgtgtatatcacagacaaaactgtgctagacatgaggtct
atggacttcaagagcaacagtgctgtggcctggagcaacaaatctgactttgcatgtgcaaacgccttcaacaacagcattat
tccagaagacaccttcttccccagcccagaaagttcctgtgatgtcaagctggtcgagaaaagctttgaaacagatacgaac
ctaaactttcaaaacctgtcagtgattgggttccgaatcctcctcctgaaagtggccgggtttaatctgctcatgacgctgcgg
ctgtggtccagc (SEQ ID NO.4)

Fig. 1D

METLLGLLILWLQLQWVSSKQEVTQIPAALSVPEGENLVLNCSFTDSAIYNLQW
FRQDPGKGLTSLLLIQSSQREQTSGRLNASLDKSSGRSTLYIAASQPGDSATYLC
AVNSGGSNYKLTFGKGTLLTVNPNIQNPDPAVYQLRDSKSSDKSVCLFTDFDSQ
TNVSQSKDSDVYITDKTVLDMRSMDFKSNSAVAWSNKSDFACANAFNNSIIPE
DTFFPSPESSCDVKLVEKSFETDTNLNFQNLSVIGFRILLLKVAGFNLLMTLRLW
SS (SEQ ID NO.22)

Fig. 1E atggagaccctcttgggcctgcttatcctttggctgcagctgcaatgggtgagcagcaaacaggaggtgacacagattcctg cagctctgagtgtcccagaaggagaaaacttggttctcaactgcagtttcactgatagcgctatttacaacctccagtggttta ggcaggaccctgggaaaggtctcacatctctgttgcttattcagtcaagtcagagagagcaaacaagtggaagacttaatgc ctcgctggataaatcatcaggacgtagtactttatacattgcagcttctcagcctggtgactcagccacctacctctgtgctgtg aatagtggaggtagcaactataaactgacatttggaaaaggaactctcttaaccgtgaatccaaatAtccagaaccctgacc ctgccgtgtaccagctgagagactctaaatccagtgacaagtctgtctgcctattcaccgatttttgattctcaaacaaatgtgtc acaaagtaaggattctgatgtgtatatcacagacaaaactgtgctagacatgaggtctatggacttcaagagcaacagtgctg tggcctggagcaacaaatctgactttgcatgtgcaaacgccttcaacaacagcattattccagaagacaccttcttccccagc ccagaaagttcctgtgatgtcaagctggtcgagaaaagctttgaaacagatacgaacctaaactttcaaaacctgtcagtgatt gggttccgaatcctcctcctgaaagtggccgggtttaatctgctcatgacgctgcggctgtggtccagc (SEQ ID NO.23)

Fig. 1F

GAGVSQSPRYKVAKRGQDVALRCDPISGHVSLFWYQQALGQGPEFLTYFQNEA
QLDKSGLPSDRFFAERPEGSVSTLKIQRTQQEDSAVYLCASSLFGQGREKLFFGS
GTQLSVL (SEQ ID NO.5)

Fig. 2A ggtgctggagtctcccagtcccctaggtacaaagtcgcaaagagaggacaggatgtagctctcaggtgtgatccaatttcgg
gtcatgtatcccttttttggtaccaacaggccctggggcaggggccagagtttctgacttatttccagaatgaagctcaactag
acaaatcggggctgcccagtgatcgcttctttgcagaaaggcctgagggatccgtctccactctgaagatccagcgcacac
agcaggaggactccgccgtgtatctctgtgccagcagcttattcgggcagggacgggaaaaactgttttttggcagtggaac
ccagctctctgtcttg (SEQ ID NO.6)

Fig. 2B

GAGVSQSPRYKVAKRGQDVALRCDPISGHVSLFWYQQALGQGPEFLTYFQNEA
QLDKSGLPSDRFFAERPEGSVSTLKIQRTQQEDSAVYLCASSLFGQGREKLFFGS
GTQLSVLEDLNKVFPPEVAVFEPSEAEISHTQKATLVCLATGFFPDHVELSWWV
NGKEVHSGVSTDPQPLKEQPALNDSRYCLSSRLRVSATFWQNPRNHFRCQVQF
YGLSENDEWTQDRAKPVTQIVSAEAWGRADCGFTSVSYQQGVLSATILYEILL
GKATLYAVLVSALVLMAMVKRKDF (SEQ ID NO.7)

Fig. 2C ggtgctggagtctcccagtcccctaggtacaaagtcgcaaagagaggacaggatgtagctctcaggtgtgatccaatttcgg
gtcatgtatcccttttttggtaccaacaggccctggggcaggggccagagtttctgacttatttccagaatgaagctcaactag
acaaatcggggctgcccagtgatcgcttctttgcagaaaggcctgagggatccgtctccactctgaagatccagcgcacac
agcaggaggactccgccgtgtatctctgtgccagcagcttattcgggcagggacgggaaaaactgttttttggcagtggaac
ccagctctctgtcttgGaggacctgaacaaggtgttcccacccgaggtcgctgtgtttgagccatcagaagcagagatctcc
cacacccaaaaggccacactggtgtgcctggccacaggcttcttccccgaccacgtggagctgagctggtgggtgaatgg
gaaggaggtgcacagtggggtcagcacggacccgcagcccctcaaggagcagcccgccctcaatgactccagatactg
cctgagcagccgcctgagggtctcggccaccttctggcagaaccccgcaaccacttccgctgtcaagtccagttctacgg
gctctcggagaatgacgagtggacccaggatagggccaaacccgtcacccagatcgtcagcgccgaggcctggggtag
agcagactgtggctttacctcggtgtcctaccagcaaggggtcctgtctgccaccatcctctatgagatcctgctagggaag
gccaccctgtatgctgtgctggtcagcgcccttgtgttgatggccatggtcaagagaaaggatttc
(SEQ ID NO.8)

Fig. 2D

MGTRLLCWVVLGFLGTDHTGAGVSQSPRYKVAKRGQDVALRCDPISGHVSLF
WYQQALGQGPEFLTYFQNEAQLDKSGLPSDRFFAERPEGSVSTLKIQRTQQEDS
AVYLCASSLFGQGREKLFFGSGTQLSVLEDLNKVFPPEVAVFEPSEAEISHTQKA
TLVCLATGFFPDHVELSWWVNGKEVHSGVSTDPQPLKEQPALNDSRYCLSSRL
RVSATFWQNPRNHFRCQVQFYGLSENDEWTQDRAKPVTQIVSAEAWGRADCG
FTSVSYQQGVLSATILYEILLGKATLYAVLVSALVLMAMVKRKDF (SEQ ID NO.24)

Fig. 2E

Atgggcaccaggctcctctgctgggtggtcctgggtttcctagggacagatcacacaggtgctggagtctcccagtcccct
aggtacaaagtcgcaaagagaggacaggatgtagctctcaggtgtgatccaatttcgggtcatgtatccttttttggtaccaa
caggccctggggcaggggccagagtttctgacttatttccagaatgaagctcaactagacaaatcggggctgcccagtgat
cgcttctttgcagaaaggcctgagggatccgtctccactctgaagatccagcgcacacagcaggaggactccgccgtgtat
ctctgtgccagcagcttattcgggcagggacgggaaaaactgttttttggcagtggaacccagctctctgtcttgGaggacc
tgaacaaggtgttcccacccgaggtcgctgtgtttgagccatcagaagcagagatctcccacacccaaaaggccacactgg
tgtgcctggccacaggcttcttccccgaccacgtggagctgagctggtgggtgaatgggaaggaggtgcacagtggggtc
agcacggacccgcagcccctcaaggagcagcccgccctcaatgactccagatactgcctgagcagccgcctgagggtct
cggccaccttctggcagaaccccgcaaccacttccgctgtcaagtccagttctacgggctctcggagaatgacgagtgga
cccaggatagggccaaaccgtcacccagatcgtcagcgccgaggcctggggtagagcagactgtggctttacctcggtg
tcctaccagcaaggggtcctgtctgccaccatcctctatgagatcctgctagggaaggccaccctgtatgctgtgctggtcag
cgcccttgtgttgatggccatggtcaagagaaaggatttc (SEQ ID NO.25)

Fig. 2F

MKQEVTQIPAALSVPEGENLVLNCSFTDSAIYNLQWFRQDPGKGLTSLLLIQSSQ
REQTSGRLNASLDKSSGRSTLYIAASQPGDSATYLCAVNSGGSNYKLTFGKGTL
LTVNPNIQNPDPAVYQLRDSKSSDKSVCLFTDFDSQTNVSQSKDSDVYITDKCV
LDMRSMDFKSNSAVAWSNKSDFACANAFNNSIIPEDTFFPSPESS (SEQ ID NO.26)

Fig. 4A

ATGAAACAGGAAGTGACCCAGATTCCTGCAGCTCTGAGTGTCCCAGAAGGA
GAAAACTTGGTTCTCAACTGCAGTTTCACTGATAGCGCTATTTACAACCTCC
AGTGGTTTAGGCAGGACCCTGGGAAGGTCTCACATCTCTGTTGCTTATTCA
GTCAAGTCAGAGAGAGCAAACAAGTGGAAGACTTAATGCCTCGCTGGATAA
ATCATCAGGACGTAGTACTTTATACATTGCAGCTTCTCAGCCTGGTGACTCA
GCCACCTACCTCTGTGCTGTGAATAGTGGAGGTAGCAACTATAAACTGACAT
TTGGAAAAGGAACTCTCTTAACCGTGAATCCAAATATCCAGAACCCTGACCC
TGCCGTGTACCAGCTGAGAGACTCTAAGTCGAGTGACAAGTCTGTCTGCCTA
TTCACCGATTTTGATTCTCAAACAAATGTGTCACAAAGTAAGGATTCTGATG
TGTATATCACAGACAAATGTGTGCTAGACATGAGGTCTATGGACTTCAAGA
GCAACAGTGCTGTGGCCTGGAGCAACAAATCTGACTTTGCATGTGCAAACG
CCTTCAACAACAGCATTATTCCAGAAGCACCTTCTTCCCCAGCCCAGAAAG
TTCC (SEQ ID NO.27)

Fig. 4B

MGAGVSQSPRYKVAKRGQDVALRCDPISGHVSLFWYQQALGQGPEFLTYFQN
EAQLDKSGLPSDRFFAERPEGSVSTLKIQRTQQEDSAVYLCASSLFGQGREKLFF
GSGTQLSVLEDLKNVFPPEVAVFEPSEAEISHTQKATLVCLATGFYPDHVELSW
WVNGKEVHSGVCTDPQPLKEQPALNDSRYALSSRLRVSATFWQDPRNHFRCQ
VQFYGLSENDEWTQDRAKPVTQIVSAEAWGRAD (SEQ ID NO.28)

Fig. 5A

ATGGGTGCAGGTGTTAGCCAGTCCCCTAGGTACAAAGTCGCAAAGAGAGGA
CAGGATGTAGCTCTCAGGTGTGATCCAATTTCGGGTCATGTATCCCTTTTTG
GTACCAACAGGCCCTGGGGCAGGGGCCAGAGTTTCTGACTTATTTCCAGAAT
GAAGCTCAACTAGACAAATCGGGGCTGCCCAGTGATCGCTTCTTTGCAGAA
AGGCCTGAGGGATCCGTCTCCACTCTGAAGATCCAGCGCACACAGCAGGAG
GACTCCGCCGTGTATCTCTGTGCCAGCAGCTTATTCGGGCAGGGACGGGAA
AAACTGTTTTTTGGCAGTGGAACCCAGCTCTCTGTCTTGGAGGACCTGAAAA
ACGTGTTCCCACCCGAGGTCGCTGTGTTTGAGCCATCAGAAGCAGAGATCTC
CCACACCCAAAAGGCCACACTGGTGTGCCTGGCCACCGGTTTCTACCCCGAC
CACGTGGAGCTGAGCTGGTGGGTGAATGGGAAGGAGGTGCACAGTGGGGTC
TGCACAGACCCGCAGCCCCTCAAGGAGCAGCCCGCCCTCAATGACTCCAGA
TACGCTCTGAGCAGCCGCCTGAGGGTCTCGGCCACCTTCTGGCAGGACCCCC
GCAACCACTTCCGCTGTCAAGTCCAGTTCTACGGGCTCTCGGAGAATGACGA
GTGGACCCAGGATAGGGCCAAACCCGTCACCCAGATCGTCAGCGCCGAGGC
CTGGGGTAGAGCAGAC (SEQ ID NO.29)

Fig. 5B

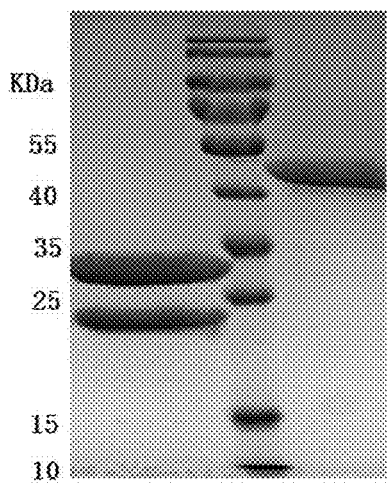

Fig. 6

AKQEVTQSPASLSVPEGENVSINCSFTDSAIYNLQWFRQDPGKGLTSLLLIQSSQ
REQTSGRLNASLDKSSGRSTLYIEDVQPGDSATYLCAVNSGGSNYKLTFGKGTK
LTVNPGGGSEGGGSEGGGSEGGGSEGGTGGAGVSQSPRYLSVKRGQDVTLRCD
PISGHVSLFWYQQAPGQGPEFLTYFQNEAQLDKSGLPSDRFFAERPEGSVSTLKI
QRVQPEDSAVYLCASSLFGQGREKLFFGSGTQLSVD (SEQ ID NO.30)

Fig. 7A

GCTAAACAAGAAGTTACTCAAAGCCCGGCGAGCCTGAGCGTGCCGGAGGGT
GAAAACGTTAGCATCAACTGCAGCTTCACCGACAGCGCGATTTACAACCTG
CAATGGTTTCGTCAGGACCCGGGCAAGGGCCTGACCAGCCTGCTGCTGATCC
AGAGCAGCCAACGTGAGCAGACCAGCGGTCGTCTGAACGCGAGCCTGGACA
AAAGCAGCGGCCGTAGCACCCTGTATATTGAAGACGTGCAACCGGGTGATA
GCGCGACCTACCTGTGCGCGGTTAACAGCGGTGGCAGCAACTATAAGCTGA
CCTTTGGCAAGGGCACCAAACTGACCGTTAACCCGGGTGGCGGTAGCGAGG
GCGGTGGCAGCGAAGGTGGCGGTAGCGAGGGCGGTGGCAGCGAAGGTGGC
ACCGGTGGCGCGGGTGTGAGCCAAAGCCCGCGTTACCTGAGCGTGAAACGT
GGTCAGGACGTTACCCTGCGTTGCGATCCGATCAGCGGCCACGTTAGCCTGT
TCTGGTATCAGCAAGCGCCGGGTCAGGGTCCGGAGTTCCTGACCTATTTTCA
AAACGAAGCGCAGCTGGACAAGAGCGGTCTGCCGAGCGATCGTTTCTTTGC
GGAGCGTCCGGAAGGCAGCGTGAGCACCCTGAAAATTCAACGTGTGCAGCC
GGAGGACAGCGCGGTTTATCTGTGCGCGAGCAGCCTGTTTGGTCAAGGCCG
TGAAAAACTGTTCTTTGGTAGCGGCACCCAGCTGAGCGTTGAT
(SEQ ID NO.31)

Fig. 7B

AKQEVTQSPASLSVPEGENVSINCSFTDSAIYNLQWFRQDPGKGLTSLLLIQSSQ
REQTSGRLNASLDKSSGRSTLYIEDVQPGDSATYLCAVNSGGSNYKLTFGKGTK
LTVNP (SEQ ID NO.32)

Fig. 8A

GCTAAACAAGAAGTTACTCAAAGCCCGGCGAGCCTGAGCGTGCCGGAGGGT
GAAAACGTTAGCATCAACTGCAGCTTCACCGACAGCGCGATTTACAACCTG
CAATGGTTTCGTCAGGACCCGGGCAAGGGCCTGACCAGCCTGCTGCTGATCC
AGAGCAGCCAACGTGAGCAGACCAGCGGTCGTCTGAACGCGAGCCTGGACA
AAAGCAGCGGCCGTAGCACCCTGTATATTGAAGACGTGCAACCGGGTGATA
GCGCGACCTACCTGTGCGCGGTTAACAGCGGTGGCAGCAACTATAAGCTGA
CCTTTGGCAAGGGCACCAAACTGACCGTTAACCCG (SEQ ID NO.33)

Fig. 8B

AGVSQSPRYLSVKRGQDVTLRCDPISGHVSLFWYQQAPGQGPEFLTYFQNEAQ
LDKSGLPSDRFFAERPEGSVSTLKIQRVQPEDSAVYLCASSLFGQGREKLFFGSG
TQLSVD (SEQ ID NO.34)

Fig. 9A

GCGGGTGTGAGCCAAAGCCCGCGTTACCTGAGCGTGAAACGTGGTCAGGAC
GTTACCCTGCGTTGCGATCCGATCAGCGGCCACGTTAGCCTGTTCTGGTATC
AGCAAGCGCCGGGTCAGGGTCCGGAGTTCCTGACCTATTTTCAAAACGAAG
CGCAGCTGGACAAGAGCGGTCTGCCGAGCGATCGTTTCTTTGCGGAGCGTCC
GGAAGGCAGCGTGAGCACCCTGAAAATTCAACGTGTGCAGCCGGAGGACAG
CGCGGTTTATCTGTGCGCGAGCAGCCTGTTTGGTCAAGGCCGTGAAAAACTG
TTCTTTGGTAGCGGCACCCAGCTGAGCGTTGAT (SEQ ID NO.35)

Fig. 9B

GGGSEGGGSEGGGSEGGGSEGGTGG (SEQ ID NO.36)

Fig. 10A

GGTGGCGGTAGCGAGGGCGGTGGCAGCGAAGGTGGCGGTAGCGAGGGCGG
TGGCAGCGAAGGTGGCACCGGTGGC (SEQ ID NO.37)

Fig. 10B

T CELL RECEPTOR FOR IDENTIFYING AFP ANTIGEN

TECHNICAL FIELD

The present invention relates to TCRs capable of recognizing short peptides derived from AFP antigens. The present invention also relates to AFP-specific T cells obtained by transducing the above-mentioned TCRs, and uses thereof in the prevention and treatment of AFP-related diseases.

BACKGROUND

AFP, also known as a fetoprotein, is a protein expressed during embryonic development and the main component of embryonic serum. During development, there is a relatively high expression level of AFP in the yolk sac and liver, which is subsequently inhibited. In hepatocellular carcinoma, the expression of AFP is activated (Butterfield et al. J Immunol., 2001, Apr. 15; 166(8): 5300-8). After produced in the cell, AFP is degraded into small molecular peptides, and combined with MHC (major histocompatibility complex) molecules to form a complex, which is presented to the cell surface. FMNKFIYEI (SEQ ID NO: 9) is a short peptide derived from AFP antigen and a target for treating AFP-related diseases.

T cell adoptive immunotherapy is to transfer reactive T cells specific to target cell antigens into a patient's body so that they can act against the target cells. T cell receptor (TCR) is a membrane protein on the surface of T cells that can recognize antigen short peptides on the surface of corresponding target cells. In the immune system, the combination of antigen short peptide-specific TCR and short peptide-major histocompatibility complex (pMHC complex) will induce the direct physical contact between T cells and antigen presenting cells (APC), and then other cell membrane surface molecules of T cells and APC interact with each other, causing a series of subsequent cell signaling and other physiological reactions, so that T cells with different antigen specificities can exert immune effects on target cells thereof. Therefore, a skilled person are dedicated to isolating TCRs specific to AFP antigen short peptides, and transducing the TCR to T cells to obtain T cells specific to AFP antigen short peptides, so that they can play a role in cellular immunotherapy.

SUMMARY OF THE INVENTION

The purpose of the present invention is to provide a T cell receptor that recognizes short peptides of AFP antigen.

In the first aspect of the present invention, a T cell receptor (TCR) that can bind to the FMNKFIYEI-HLA A0201 complex is provided.

In another preferred embodiment, the TCR comprises a TCR α chain variable domain and a TCR β chain variable domain, and the amino acid sequence of CDR3 of the TCR α chain variable domain is AVNSGGSNYKLT (SEQ ID NO: 12); and/or the the amino acid sequence of CDR3 of the TCR β chain variable domain is ASSLFGQGREKLF (SEQ ID NO: 15).

In another preferred embodiment, 3 complementarity determining regions (CDR) of the TCR α chain variable domain are:

```
                                        (SEQ ID NO: 10)
        α CDR1- DSAIYN
                                        (SEQ ID NO: 11)
        α CDR2- IQSSQRE
                                        (SEQ ID NO: 12)
        α CDR3- AVNSGGSNYKLT;
``` and/or
3 complementarity determining regions of the TCR β chain variable domain are:

```
                                        (SEQ ID NO: 13)
        β CDR1- SGHVS
                                        (SEQ ID NO: 14)
        β CDR2- FQNEAQ
                                        (SEQ ID NO: 15)
        β CDR3- ASSLFGQGREKLF.
```

In another preferred embodiment, the TCR comprises a TCR α chain variable domain and a TCR β chain variable domain, and the TCR α chain variable domain is an amino acid sequence having at least 90% sequence identity with SEQ ID NO: 1; and/or the TCR β chain variable domain is an amino acid sequence with at least 90% sequence identity with SEQ ID NO: 5.

In another preferred embodiment, the TCR comprises a TCR α chain variable domain, the amino acid sequence of which is SEQ ID NO: 1.

In another preferred embodiment, the TCR comprises a TCR β chain variable domain, the amino acid sequence of which is SEQ ID NO: 5.

In another preferred embodiment, the TCR is a αβ heterodimer, which comprises a TCR α chain constant region TRAC*01 and a TCR β chain constant region TRBC1*01 or TRBC2*01.

In another preferred embodiment, the amino acid sequence of the TCR α chain is SEQ ID NO: 3 and/or the amino acid sequence of the TCR β chain is SEQ ID NO: 7.

In another preferred embodiment, the TCR is soluble.

In another preferred embodiment, the TCR is a single-chain TCR.

In another preferred embodiment, the TCR is formed by connecting the α chain variable domain and the β chain variable domain through a peptide linking sequence.

In another preferred embodiment, the TCR has one or more mutations at amino acid position 11, 13, 19, 21, 53, 76, 89, 91, or 94 of the α chain variable region, and/or at the last 3, 5 or 7 amino acid position of the short peptide of the α chain J gene; and/or the TCR has one or more mutations at amino acid position 11, 13, 19, 21, 53, 76, 89, 91, or 94 of the β chain variable region, and/or at the last 2, 4, or 6 amino acid position of the short peptide of the β chain J gene, wherein the amino acid position number is based on the position number listed in IMGT (International Immunogenetics Information System).

In another preferred embodiment, the amino acid sequence of the α chain variable domain of the TCR comprises SEQ ID NO: 32 and/or the amino acid sequence of the β chain variable domain of the TCR comprises SEQ ID NO: 34.

In another preferred embodiment, the amino acid sequence of the TCR is SEQ ID NO: 30.

In another preferred embodiment, the TCR comprises (a) all or part of the TCR α chain except for its transmembrane domain, and (b) all or part of the TCR β chain except for its transmembrane domain;

and each of (a) and (b) comprise the functional variable domain, or the functional variable domain and at least a portion of the constant domain of the TCR chain, respectively.

In another preferred embodiment, cysteine residues form an artificial disulfide bond between the α and β chain constant domains of the TCR.

In another preferred embodiment, the cysteine residues forming the artificial interchain disulfide bond in the TCR are substituted for one or more groups of amino acids selected from the following:

Thr48 of TRAC*01 exon 1 and Ser57 of TRBC1*01 or TRBC2*01 exon 1;

Thr45 of TRAC*01 exon 1 and Ser77 of TRBC1*01 or TRBC2*01 exon 1;

Tyr10 of TRAC*01 exon 1 and Ser17 of TRBC1*01 or TRBC2*01 exon 1;

Thr45 of TRAC*01 exon 1 and Asp59 of TRBC1*01 or TRBC2*01 exon 1;

Ser15 of TRAC*01 exon 1 and Glu15 of TRBC1*01 or TRBC2*01 exon 1;

Arg53 of TRAC*01 exon 1 and Ser54 of TRBC1*01 or TRBC2*01 exon 1;

Pro89 of TRAC*01 exon 1 and Ala19 of TRBC1*01 or TRBC2*01 exon 1; and

Tyr10 of TRAC*01 exon 1 and Glu20 of TRBC1*01 or TRBC2*01 exon 1.

In another preferred embodiment, the amino acid sequence of the TCR α chain is SEQ ID NO: 26 and/or the amino acid sequence of the TCR β chain is SEQ ID NO: 28.

In another preferred embodiment, an artificial interchain disulfide bond is contained between α chain variable region and β chain constant region of the TCR.

In another preferred embodiment, cysteine residues forming the artificial interchain disulfide bond in the TCR are substituted for one or more groups of amino acids selected from the following:

amino acid at position 46 of TRAV and amino acid at position 60 of TRBC1*01 or TRBC2*01 exon 1;

amino acid at position 47 of TRAV and amino acid at position 61 of TRBC1*01 or TRBC2*01 exon 1;

amino acid at position 46 of TRAV and amino acid at position 61 of TRBC1*01 or TRBC2*01 exon 1; or amino acid at position 47 of TRAV and amino acid at position 60 of TRBC1*01 or TRBC2*01 exon 1.

In another preferred embodiment, the TCR comprises α chain variable domain and β chain variable domain as well as all or part of β chain constant domains except for its transmembrane domain, however it does not comprise α chain constant domain, and α chain variable domain and β chain of the TCR form a heterodimer.

In another preferred embodiment, a conjugate binds to the α chain and/or β chain of the TCR at C- or N-terminal.

In another preferred embodiment, the conjugate that binds to the TCR is a detectable label, a therapeutic agent, a PK modified moiety, or a combination thereof. Preferably, the therapeutic agent is an anti-CD3 antibody.

In the second aspect of the invention, a multivalent TCR complex is provided, wherein the multivalent TCR complex comprises at least two TCR molecules, and at least one TCR molecule is the TCR of the first aspect of the invention.

In the third aspect of the invention, a nucleic acid molecule is provided, comprising a nucleic acid sequence encoding the TCR molecule of the first aspect of the invention, or a complement sequence thereof.

In another preferred embodiment, the nucleic acid molecule comprises the nucleotide sequence SEQ ID NO: 2 or SEQ ID NO: 33 encoding the variable domain of the TCR α chain.

In another preferred embodiment, the nucleic acid molecule comprises the nucleotide sequence SEQ ID NO: 6 or SEQ ID NO: 35 encoding the variable domain of the TCR β chain.

In another preferred embodiment, the nucleic acid molecule comprises the nucleotide sequence SEQ ID NO: 4 encoding the TCR α chain and/or the nucleotide sequence SEQ ID NO: 8 encoding the variable domain of the TCR β chain.

In the fourth aspect of the invention, a vector is provided, comprising the nucleic acid molecule of the third aspect of the invention; preferably, the vector is a viral vector; and more preferably, the vector is a lentiviral vector.

In the fifth aspect of the present invention, an isolated host cell is provided, comprising the vector of the fourth aspect of the present invention or having the exogenous nucleic acid molecule of the third aspect of the present invention integrated into its genome.

In the sixth aspect of the invention, a cell is provided, which is transduced with the nucleic acid molecule of the third aspect of the present invention or the vector of the fourth aspect of the invention; and preferably, the cell is a T cell or stem cell.

In the seventh aspect of the invention, a pharmaceutical composition is provided, comprising a pharmaceutically acceptable carrier, and the TCR of the first aspect of the invention, or the TCR complex of the second aspect of the invention, the nucleic acid molecule of the third aspect of the present invention, the vector of the fourth aspect of the invention, or the cell of the sixth aspect of the invention.

In the eighth aspect of the invention, use of the TCR of the first aspect of the invention, or the TCR complex of the second aspect of the invention, the nucleic acid molecule of the third aspect of the present invention, the vector of the fourth aspect of the invention, or the cell of the sixth aspect of the invention is provided for preparing a medicament for treating tumor or autoimmune disease.

In an ninth aspect of the present invention, a method for treating a disease is provided, comprising administering an appropriate amount of the TCR of the first aspect of the present invention, the TCR complex of the second aspect of the present invention, the nucleic acid molecule of the third aspect of the present invention, the vector of the fourth aspect of the invention, the cell of the sixth aspect of the invention, or the pharmaceutical composition of the seventh aspect of the invention to a subject in need thereof;

Preferably, the disease is a tumor, and preferably, the tumor is Hepatocellular carcinoma.

It is to be understood that within the scope of the present invention, the various technical features of the present invention and the technical features specifically described hereinafter (as in the embodiments) may be combined with each other to constitute a new or preferred technical solution, which will not be repeated herein one by one.

DESCRIPTION OF DRAWINGS

FIG. 1A, FIG. 1B, FIG. 1C, FIG. 1D, FIG. 1E and FIG. 1F are the amino acid sequence of the TCR α chain variable domain, the nucleotide sequence of the TCR α chain variable domain, the amino acid sequence of the TCR α chain, the nucleotide sequence of the TCR α chain, the amino acid sequence of the TCR α chain with the leader sequence and the nucleotide sequence of the TCR α chain with the leader sequence.

FIG. 2A, FIG. 2B, FIG. 2C, FIG. 2D, FIG. 2E and FIG. 2F are the amino acid sequence of the TCR β chain variable domain, the nucleotide sequence of the TCR β chain variable domain, the amino acid sequence of the TCR β chain, the nucleotide sequence of the TCR β chain, the amino acid sequence of the TCR β chain with the leader sequence and the nucleotide sequence of the TCR β chain with the leader sequence.

FIG. 4A and FIG. 4B are the amino acid sequence and nucleotide sequence of the soluble TCR α chain, respectively.

FIG. 5A and FIG. 5B are the amino acid sequence and nucleotide sequence of the soluble TCR β chain, respectively.

FIG. 6 is a gel image of soluble TCR obtained after purification. The leftmost lane is the reducing gel, the middle lane is the molecular weight marker, and the right lane is the non-reducing gel.

FIG. 7A and FIG. 7B are the amino acid sequence and nucleotide sequence of the single-chain TCR, respectively.

FIG. 8A and FIG. 8B are the amino acid sequence and nucleotide sequence of the variable domain of the single-chain TCR α chain, respectively.

FIG. 9A and FIG. 9B are the amino acid sequence and nucleotide sequence of the variable domain of the single-chain TCR β chain, respectively.

FIG. 10A and FIG. 10B are the amino acid sequence and nucleotide sequence of the linker of the single-chain TCR, respectively.

MODES FOR CARRYING OUT THE INVENTION

Figure 3:
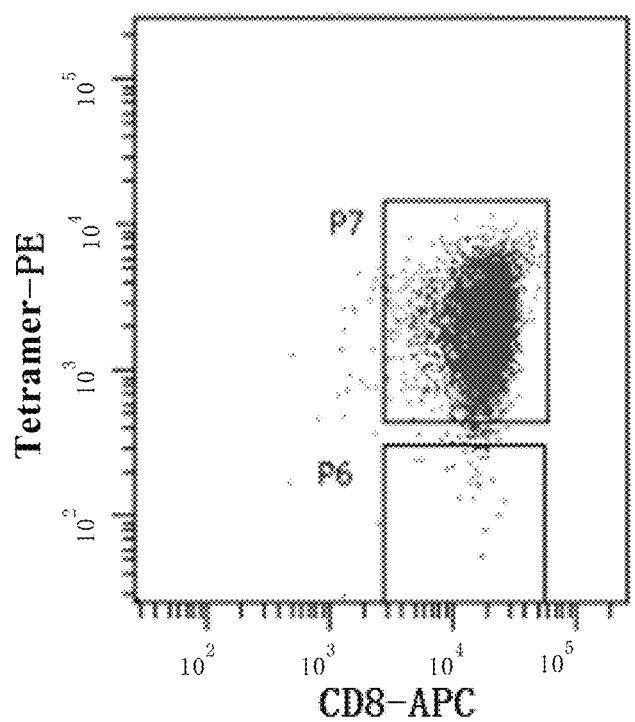
FIG. 3 shows the CD8$^+$ and tetramer-PE double positive staining results of monoclonal cells.

After extensive and in-depth research, the inventors found a TCR that can specifically bind to the AFP antigen short peptide FMNKFIYEI (SEQ ID NO: 9). The antigen short peptide FMNKFIYEI can form a complex with HLA A0201 and be presented together to the cell surface. The present invention also provides a nucleic acid molecule encoding the TCR and a vector containing the nucleic acid molecule. In addition, the present invention also provides cells transduced with the TCR of the present invention.

Term

MHC molecules are proteins of the immunoglobulin superfamily, and can be MHC molecules of class I or class II. Therefore, it is specific for the presentation of antigens. Different individuals have different MHCs and can present different short peptides in a protein antigen to the surface of respective APC cells thereof. Human MHC is usually called HLA gene or HLA complex.

T cell receptor (TCR) is the only receptor for presenting specific peptide antigens in Major Histocompatibility Complex (MHC). The exogenous or endogenous peptides may be the only sign of abnormality in a cell. In the immune system, direct physical contact of a T-cell and an antigen presenting cell (APC) will be initiated by the binding of antigen-specific TCRs to pMHC complexes. Then, the interaction of other membrane molecules in T cell and APC occurs and the subsequent cell signaling and other physiological responses are initiated so that a range of different antigen-specific T cells exert immune effects on their target cells.

TCR is a glycoprotein on the surface of the cell membrane existing as a heterodimer of α chain/β chain or γ chain/δ chain. In 95% of T cells, TCR heterodimers consist of α and β chains, while 5% of T cells have TCRs consisting of γ and δ chains. Natural αβ heterodimeric TCR has α chain and β chain, and α chain and β chain constitute subunits of αβ heterodimeric TCR. Generally speaking, each of α and β chains includes a variable region, a connecting region and a constant region. The β chain usually also comprises a short variable region between the variable region and the connecting region, but the variable region is often regarded as a part of the connecting region. Each variable region comprises 3 CDRs (complementarity determining regions), CDR1, CDR2, and CDR3 embedded in framework regions. The CDR regions determine the binding of TCR to pMHC complex, wherein CDR3 is formed from recombination of the variable region and the connecting region, and called the hypervariable region. The α and β chains of a TCR are generally regarded as having two "domains" respectively, namely a variable domain and a constant domain. The variable domain consists of a connected variable region and a connecting region. The sequence of the constant domain of a TCR can be found in the public database of the International Immunogenetics Information System (IMGT). For example, the sequence of the constant domain of the α chain of a TCR molecule is "TRAC*01", and the sequence of the constant domain of the β chain of a TCR molecule is "TRBC1*01" or "TRBC2*01". In addition, the α and β chains of a TCR also comprise transmembrane region and cytoplasmic region, which are very short.

In the present invention, the terms "polypeptide of the present invention", "TCR of the present invention", and "T cell receptor of the present invention" are used interchangeably.

Natural Inter-Chain Disulfide Bond and Artificial Inter-Chain Disulfide Bond

A group of disulfide bonds is present between the Cα and Cβ chains in the membrane proximal region of a native TCR, which is named herein as "natural inter-chain disulfide bond". In the present invention, an inter-chain covalent disulfide bond which is artificially introduced and the position of which is different from the position of a natural inter-chain disulfide bond is named as "artificial inter-chain disulfide bond".

For conveniently describing the position of disulfide bond, in the present invention, the positions of the amino acid sequences of TRAC*01 and TRBC1*01 or TRBC2*01 are sequentially numbered in order from N-terminal to C-terminal. For example, the $60^{th}$ amino acid in the order from N-terminal to C-terminal in TRBC1*01 or TRBC2*01 is P (valine), which can be described as Pro60 of TRBC1*01 or TRBC2*01 exon 1 in the present invention, and can also be expressed as the amino acid at position 60 of TRBC1*01 or TRBC2*01 exon 1. For another example, the 61$^{st}$ amino acid in the order from N-terminal to C-terminal in TRBC1*01 or TRBC2*01 is Q (glutamine), which can be described as Gln61 of TRBC1*01 or TRBC2*01 exon 1 in the invention, and can also be expressed as the amino acid at position 61 of TRBC1*01 or TRBC2*01 exon 1, and so on. In the present invention, the positions of the amino acid sequences of variable regions TRAV and TRBV are numbered according to the positions listed in IMGT. As for an amino acid in TRAV, the position is numbered as 46 in IMGT, which is described in the present invention as the amino acid at position 46 of TRAV, and so on. In the present invention, if the sequence positions of other amino acids are specifically described, the special description shall prevail.

DETAILED DESCRIPTION OF THE INVENTION

TCR Molecule

In the process of antigen processing, the antigen is degraded inside the cell and then carried to the cell surface by MHC molecules. T cell receptors can recognize peptide-MHC complexes on the surface of antigen-presenting cells. Therefore, in the first aspect of the present invention, a TCR molecule capable of binding to the FMNKFIYEI-HLA A0201 complex is provided. Preferably, the TCR molecule is isolated or purified. Each of the α and β chains of the TCR has three complementarity determining regions (CDR).

In a preferred embodiment of the present invention, the α chain of the TCR includes CDRs having the following amino acid sequences:

```
                                    (SEQ ID NO: 10)
        α CDR1- DSAIYN (SEQ ID NO: 11)
        α CDR2- IQSSQRE (SEQ ID NO: 12)
        α CDR3- AVNSGGSNYKLT;
``` and/or 3 complementarity determining regions of the TCR β chain variable domain are:

```
                                    (SEQ ID NO: 13)
        β CDR1- SGHVS (SEQ ID NO: 14)
        β CDR2- FQNEAQ (SEQ ID NO: 15)
        β CDR3- ASSLFGQGREKLF.
```

The above amino acid sequences of the CDR regions of the present invention can be embedded into any suitable framework structure to prepare a chimeric TCR. As long as the framework structure is compatible with the CDR regions of the TCR of the present invention, a skilled person can design or synthesize TCR molecules with corresponding functions based on the CDR regions disclosed in the present invention. Therefore, the TCR molecule of the present invention refers to a TCR molecule comprising the above-mentioned α and/or β chain CDR region sequences and any suitable framework structure. The TCR α chain variable domain of the present invention is an amino acid sequence having at least 90%, preferably 95%, and more preferably 98% sequence identity with SEQ ID NO: 1; and/or the TCR β chain variable domain of the present invention is an amino acid sequence having at least 90%, preferably 95%, more preferably 98% sequence identity with SEQ ID NO: 5.

In a preferred embodiment of the present invention, the TCR molecule of the present invention is a heterodimer consisting of α and β chains. Specifically, the α chain of the heterodimeric TCR molecule, on the one hand, comprises a variable domain and a constant domain, and the amino acid sequence of the α chain variable domain comprises CDR1 (SEQ ID NO: 10) and CDR2 (SEQ ID NO: 11) and CDR3 (SEQ ID NO: 12) of the above α chain. Preferably, the TCR molecule comprises a α chain variable domain amino acid sequence SEQ ID NO: 1. More preferably, the amino acid sequence of the α chain variable domain of the TCR molecule is SEQ ID NO: 1. On the other hand, the β chain of the heterodimeric TCR molecule comprises a variable domain and a constant domain, and the amino acid sequence of the β chain variable domain comprises CDR1 (SEQ ID NO: 13) and CDR2 (SEQ ID NO: 14) and CDR3 (SEQ ID NO: 15). Preferably, the TCR molecule comprises the β chain variable domain amino acid sequence SEQ ID NO: 5. More preferably, the amino acid sequence of the β chain variable domain of the TCR molecule is SEQ ID NO: 5.

In a preferred embodiment of the present invention, the TCR molecule of the present invention is a single-chain TCR molecule consisting of part or all of the α chain and/or part or all of the β chain. Description of single-chain TCR molecules can be found in Chung et al (1994) Proc. Natl. Acad. Sci. USA 91, 12654-12658. According to the literature, a skilled person can easily construct single-chain TCR molecules containing the CDRs of the present invention. Specifically, the single-chain TCR molecule comprises Vα, Vβ and Cβ, and is preferably connected in an order from N-terminal to C-terminal.

The amino acid sequence of the α chain variable domain of the single-chain TCR molecule comprises CDR1 (SEQ ID NO: 10) and CDR2 (SEQ ID NO: 11) and CDR3 (SEQ ID NO: 12) of the above α chain. Preferably, the single-chain TCR molecule comprises a α chain variable domain amino acid sequence SEQ ID NO: 1. More preferably, the amino acid sequence of the α chain variable domain of the single-chain TCR molecule is SEQ ID NO: 1. The amino acid sequence of the β chain variable domain of the single-chain TCR molecule comprises CDR1 (SEQ ID NO: 13) and CDR2 (SEQ ID NO: 14) and CDR3 (SEQ ID NO: 15). Preferably, the single-chain TCR molecule comprises the β chain variable domain amino acid sequence SEQ ID NO: 5. More preferably, the amino acid sequence of the β chain variable domain of the single-chain TCR molecule is SEQ ID NO: 5.

In a preferred embodiment of the present invention, the constant domain of the TCR molecule of the present invention is a human constant domain. A skilled person know or can obtain the amino acid sequence of the human constant domain by referring to relevant books or public databases of IMGT (International Immunogenetics Information System). For example, the constant domain sequence of the α chain of the TCR molecule of the present invention can be "TRAC*01", and the constant domain sequence of the β chain of the TCR molecule can be "TRBC1*01" or "TRBC2*01". The amino acid at 53$^{rd}$ position of the amino acid sequence given in TRAC*01 of IMGT is Arg, which is represented herein as: Arg53 of TRAC*01 exon 1, and so on. Preferably, the amino acid sequence of the α chain of the TCR molecule of the present invention is SEQ ID NO: 3, and/or the amino acid sequence of the β chain is SEQ ID NO: 7.

The naturally occurring TCR is a membrane protein that is stabilized by its transmembrane domain. Just as immunoglobulins (antibodies) which can be used as antigen recognition molecules, TCRs can also be developed for diagnosis and treatment, and it is necessary to obtain soluble TCR molecules. The soluble TCR molecule does not comprise its transmembrane region. The soluble TCR has a wide range of uses, which can be used not only to study the interaction between TCR and pMHC, but also as a diagnostic tool for detecting infections or as a marker for autoimmune diseases. Similarly, the soluble TCR can be used to deliver therapeutic agents (such as cytotoxic compounds or immunostimulatory compounds) to cells presenting specific antigens. In addition, the soluble TCR can also be combined with other molecules (such as anti-CD3 antibodies) to redirect T cells to target cells that present specific antigens. A soluble TCR specific to the AFP antigen short peptide is also obtained in the invention.

For obtaining a soluble TCR, the TCR of the present invention, on the one hand, may be a TCR in which an artificial disulfide bond is introduced between the residues of its α and β chain constant domains. Cysteine residues form an artificial interchain disulfide bond between the α and β chain constant domains of the TCR. Cysteine residues can be substituted for other amino acid residues at appropriate positions in the natural TCR to form an artificial interchain disulfide bond. For example, cysteine residues replacing Thr48 of TRAC*01 exon 1 and replacing Ser57 of TRBC1*01 or TRBC2*01 exon 1 form a disulfide bond. Other sites for introducing cysteine residues to form disulfide bonds can also be: Thr45 of TRAC*01 exon 1 and Ser77 of TRBC1*01 or TRBC2*01 exon 1; Tyr10 of TRAC*01 exon 1 and Ser17 of TRBC1*01 or TRBC2*01 exon 1; Thr45 of TRAC*01 exon 1 and Asp59 of TRBC1*01 or TRBC2*01 exon 1; Ser15 of TRAC*01 exon 1 and Glu15 of TRBC1*01 or TRBC2*01 exon 1; Arg53 of TRAC*01 exon 1 and Ser54 of TRBC1*01 or TRBC2*01 exon 1; Pro89 of TRAC*01 exon 1 and Ala19 of TRBC1*01 or TRBC2*01 exon 1; or Tyr10 of TRAC*01 exon 1 and Glu20 of TRBC1*01 or TRBC2*01 exon 1. That is, cysteine residues replace any set of positions in the constant domains of the α and β chains. A maximum of 50, or a maximum of 30, or a maximum of 15, or a maximum of 10, or a maximum of 8 or less amino acids can be truncated at one or more C-termini of the TCR constant domain of the present invention, so that it does not include Cysteine residues to achieve the purpose of deleting natural disulfide bonds, and the cysteine residues forming natural disulfide bonds can be mutated to another amino acid to achieve the above purpose.

As described above, the TCR of the present invention may comprise an artificial disulfide bond introduced between the residues of the constant domains of its α and β chains. It should be noted that, the TCR of the present invention can comprise the TRAC constant domain sequence and the TRBC1 or TRBC2 constant domain sequence regardless of whether the constant domains comprise the introduced artificial disulfide bonds as said above. The TRAC constant domain sequence and the TRBC1 or TRBC2 constant domain sequence of the TCR can be linked by natural disulfide bonds present in the TCR.

For obtaining a soluble TCR, the TCR of the present invention, on the other hand, also includes a TCR having mutations in its hydrophobic core region. These mutations in the hydrophobic core region are preferably mutations that can improve the stability of the soluble TCR of the present invention, as described in WO2014/206304. Such TCR can have a mutation in the following positions of hydrophobic core of the variable domains: amino acid position 11, 13, 19, 21, 53, 76, 89, 91, or 94 of the variable region (α and/or β chain), and/or the last 3, 5 or 7 amino acid position of the α chain J gene (TRAJ), and/or the last 2, 4, or 6 amino acid position of the β chain J gene (TRBJ), wherein the amino acid position number is based on the position number listed in IMGT (International Immunogenetics Information System). A skilled person can know the above-mentioned international immunogenetics information system, and can obtain the position numbers of the amino acid residues of different TCRs in IMGT according to the database.

In the present invention, the TCR in which the hydrophobic core region is mutated may be a stable soluble single-chain TCR consisting of the variable domains of the α and β chains of a TCR connected by a flexible peptide chain. It should be noted that the flexible peptide chain in the present invention can be any peptide chain suitable for connecting the variable domains of TCR α and β chains. For example, in the single-chain soluble TCR constructed in Example 4 of the present invention, the α chain variable domain amino acid sequence is SEQ ID NO: 32, and the encoding nucleotide sequence is SEQ ID NO: 33; β chain variable domain amino acid sequence is SEQ ID NO:34, and the encoding nucleotide sequence is SEQ ID NO:35.

In addition, in terms of stability, CN 201680003540.2 also disclosed that the introduction of an artificial interchain disulfide bond between the α chain variable region and the β chain constant region of the TCR can significantly improve the stability of the TCR. Therefore, the high-affinity TCR of the present invention may also comprise an artificial interchain disulfide bond between the α chain variable region and the β chain constant region. Specifically, cysteine residues forming an artificial interchain disulfide bond between the α chain variable region and the β chain constant region of the TCR are substituted for: amino acid at position 46 of TRAV and amino acid at position 60 of TRBC1*01 or TRBC2*01 exon 1; amino acid at position 47 of TRAV and amino acid at position 61 of TRBC1*01 or TRBC2*01 exon 1; amino acid at position 46 of TRAV and amino acid at position 61 of TRBC1*01 or TRBC2*01 exon 1; or amino acid at position 47 of TRAV and amino acid at position 60 of TRBC1*01 or TRBC2*01 exon 1. Preferably, such TCR may comprise (i) all or part of TCR α chain except for its transmembrane domain, and (ii) all or part of TCR β chain except for its transmembrane domain, wherein both of (i) and (ii) comprise the variable domain and at least a portion of constant domains of the TCR chain, and the α chain and β chain form a heterodimer. More preferably, such TCR may comprise α chain variable domain and β chain variable domain and all or part of β chain constant domain except for the transmembrane domain, which, however, does not comprise α chain constant domain, and the α chain variable domain of the TCR and the β chain form a heterodimer.

The TCR of the present invention can be provided in a form of multivalent complex. The multivalent TCR complex of the present invention comprises a polymer formed by combining two, three, four or more TCRs of the present invention, for example, a tetrameric domain of p53 can be used to produce a tetramer. Alternatively, more TCRs of the invention can be combined with another molecule to form a complex. The TCR complexes of the invention can be used to track or target cells that present a particular antigen in vitro or in vivo, or produce intermediates of other multivalent TCR complexes with such uses.

The TCR of the present invention may be used alone or combined with a conjugate in a covalent manner or other manner, preferably in a covalent manner. The conjugate includes a detectable label (for diagnostic purposes, wherein the TCR is used to detect the presence of a cell presenting FMNKFIYEI-HLA A0201 complex), a therapeutic agent, a PK (protein kinase) modifying moiety, or combination of any of the above described substances.

Detectable labels for diagnostic purposes include, but are not limited to, fluorescent or luminescent labels, radioactive labels, MRI (magnetic resonance imaging) or CT (electron computed tomography) contrast agents, or enzymes capable of producing detectable products.

Therapeutic agents that can be combined with or coupled to the TCRs of the invention include, but are not limited to: 1. Radionuclides (Koppe et al., 2005, Cancer metastasis reviews 24, 539); 2. Biotoxin (Chaudhary et al., 1989, Nature 339, 394; Epel et al., 2002, Cancer Immunology and Immunotherapy 51, 565); 3. Cytokines, such as IL-2, etc. (Gillies et al., 1992, National Academy of Sciences (PNAS) 89, 1428; Card et al., 2004, Cancer Immunology and Immunotherapy 53, 345; Halin et al., 2003, Cancer Research 63, 3202); 4. Antibody Fc fragment (Mosquera et al., 2005, The Journal Of Immunology 174, 4381); 5. Antibody scFv fragments (Zhu et al., 1995, International Journal of Cancer 62, 319); 6. Gold nanoparticles/Nanorods (Lapotko et al., 2005, Cancer letters 239, 36; Huang et al., 2006, Journal of the American Chemical Society 128, 2115); 7. Viral particles (Peng et al., 2004, Gene therapy 11, 1234); 8. Liposomes (Mamot et al., 2005, Cancer research 65, 11631); 9. Nano-magnetic particles; 10. Prodrug activating enzymes (e.g., DT-diaphorase (DTD) or biphenyl hydrolase-like protein (BPHL); 11. chemotherapeutic agent (e.g., cisplatin) or any form of nanoparticles, and the like.

In addition, the TCR of the present invention may also be a hybrid TCR containing sequences derived from more than one species. For example, studies have shown that, compared with human TCR, murine TCR can be expressed more effectively in human T cells. Therefore, the TCR of the present invention may comprise a human variable domain and a murine constant domain. The disadvantage of this method is that an immune response may be triggered. Therefore, when used in adoptive T cell therapy, there should be a regulatory scheme for immunosuppression to allow the implantation of T cells expressing murine.

It should be understood that the names of amino acids herein are represented by the internationally accepted single English letter or three English letters, and the correspondence between the single English letter and the three English letter of the names of amino acid is as follows: Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y), Val (V).

Nucleic Acid Molecule

In the second aspect of the present invention, a nucleic acid molecule encoding the TCR molecule of the first aspect of the present invention or a part thereof is provided, and the part may be one or more CDRs, variable domains of α and/or β chains, and α chains and/or β chain.

The nucleotide sequence encoding the α chain CDR region of the TCR molecule of the first aspect of the present invention is as follows:

α CDR1- gatagcgctatttacaac (SEQ ID NO: 16)

α CDR2- attcagtcaagtcagagagag (SEQ ID NO: 17)

α CDR3- gctgtgaatagtggaggtagcaactataaactgaca. (SEQ ID NO: 18)

The nucleotide sequence encoding the β chain CDR region of the TCR molecule of the first aspect of the present invention is as follows:

β CDR1- tcgggtcatgtatcc (SEQ ID NO: 19)

β CDR2- ttccagaatgaagctcaa (SEQ ID NO: 20)

β CDR3- gccagcagcttattcgggcagggacgggaaaaactgttt. (SEQ ID NO: 21)

Therefore, the nucleotide sequence of the nucleic acid molecule of the present invention encoding the TCR α chain of the present invention includes SEQ ID NO: 16, SEQ ID NO: 17 and SEQ ID NO: 18, and/or the nucleotide sequence of the nucleic acid molecule of the present invention encoding the TCR β chain of the present invention includes SEQ ID NO: 19, SEQ ID NO: 20, and SEQ ID NO: 21.

The nucleotide sequence of the nucleic acid molecule of the present invention may be of single-chain or double-chain, and the nucleic acid molecule may be RNA or DNA, and may or may not comprise introns. Preferably, the nucleotide sequence of the nucleic acid molecule of the present invention does not comprise introns but can encode the polypeptide of the present invention. For example, the nucleotide sequence of the nucleic acid molecule of the present invention encoding the variable domain of the TCR α chain of the present invention includes SEQ ID NO: 2 and/or the nucleotide sequence of the nucleic acid molecule of the present invention encoding the variable domain of the TCR β chain of the present invention includes SEQ ID NO: 6. Alternatively, the nucleotide sequence of the nucleic acid molecule of the present invention encoding the variable domain of the TCR α chain of the present invention includes SEQ ID NO: 33 and/or the nucleotide sequence of the nucleic acid molecule of the present invention encoding the variable domain of the TCR β chain of the present invention includes SEQ ID NO: 35. More preferably, the nucleotide sequence of the nucleic acid molecule of the present invention comprises SEQ ID NO: 4 and/or SEQ ID NO: 8. Alternatively, the nucleotide sequence of the nucleic acid molecule of the present invention is SEQ ID NO: 31.

It should be understood that different nucleotide sequences can encode the same polypeptide due to the degeneracy of the genetic code. Therefore, a nucleic acid sequence encoding the TCR of the invention may be the same as the nucleic acid sequence set forth in the Figures of the invention or a degenerate variant thereof. By way of one example herein, "degenerate variant" refers to a nucleic acid sequence which encodes a protein with a sequence of SEQ ID NO: 1, but is differences from the sequence of SEQ ID NO: 2.

The nucleotide sequence can be codon-optimized. Different cells are different in the use of specific codons. The codons in a sequence can be changed to increase the expression according to the cell type. Codon usage tables for mammalian cells and many other organisms are well known to a skilled person.

The full-length sequence of the nucleic acid molecule of the present invention or fragments thereof can usually be obtained by but not limited to PCR amplification method, recombination method or artificial synthesis method. At present, the DNA sequence encoding the TCR (or a fragment or derivative thereof) of the present invention can be obtained completely through chemical synthesis. This DNA sequence can then be introduced into various existing DNA molecules (or such as vectors) and cells known in the art. DNA can be a coding strand or a non-coding strand.

Vector

The invention also relates to vectors comprising the nucleic acid molecules of the invention, including expression vectors, that is, constructs that can be expressed in vivo or in vitro. Commonly used vectors include bacterial plasmids, bacteriophages, and animal and plant viruses.

Viral delivery systems include but are not limited to adenovirus vectors, adeno-associated virus (AAV) vectors, herpes virus vectors, retrovirus vectors, lentivirus vectors, and baculovirus vectors.

Preferably, the vector can transfer the nucleotide of the present invention into a cell, such as a T cell, so that the cell expresses a TCR specific for the AFP antigen. Ideally, the vector should be able to continuously express at a high level in T cells.

Cells

The invention also relates to host cells genetically engineered using the vectors or coding sequences of the invention. The host cell comprises the vector of the present invention or has the nucleic acid molecule of the present invention integrated into the chromosome. The host cell is selected from: prokaryotic cells and eukaryotic cells, such as E. coli, yeast cells, CHO cells and the like.

In addition, the invention also encompasses isolated cells, particularly T cells, expressing the TCR of the invention. The T cells may be derived from T cells isolated from a subject, or may be a mixed cell population isolated from a subject, such as a part of a peripheral blood lymphocyte (PBL) population. For example, the cells can be isolated from peripheral blood mononuclear cells (PBMC), and can be $CD4^+$ helper T cells or $CD8^+$ cytotoxic T cells. The cells can be in a mixed population of $CD4^+$ helper T cells/$CD8^+$ cytotoxic T cells. Generally, the cells can be activated with antibodies (e.g., anti-CD3 or anti-CD28 antibodies), so that they can be more easily transfected with, for example a vector containing a nucleotide sequence encoding the TCR molecule of the present invention.

Alternatively, the cells of the present invention can also be or derived from stem cells, such as hematopoietic stem cells (HSC). Transferring a gene to HSC won't result in the expression of TCR on the cell surface, since CD3 molecules are not expressed on the surface of stem cells. However, when stem cells differentiate into lymphoid precursors that migrate to the thymus, the expression of CD3 molecules will initiate the expression of the introduced TCR molecules on the surface of thymocytes.

There are a number of methods suitable for T cell transfection with DNA or RNA encoding TCR of the invention (e.g., Robbins et al., (2008) J. Immunol. 180: 6116-6131). T cells expressing the TCR of the invention can be used in adoptive immunotherapy. A skilled person can know many suitable methods for performing adoptive therapy (e.g., Rosenberg et al., (2008) Nat Rev Cancer 8(4): 299-308).

AFP Antigen-Related Disease

The present invention also relates to a method for treating and/or preventing AFP-related diseases in a subject, including a step of adoptive transferring AFP-specific T cells to the subject. The AFP-specific T cells can recognize the FMNK-FIYEI-HLA A0201 complex.

The AFP-specific T cells of the present invention can be used to treat any AFP-related diseases that present the AFP antigen short peptide FMNKFIYEI-HLA A0201 complex, including but not limited to hepatocellular carcinoma.

Treatment Method

Treatment can be carried out by isolating T cells from patients or volunteers suffering from AFP antigen-related diseases, introducing the TCR of the present invention into the above T cells, and then infusing the genetically engineered cells back into the patient. Therefore, the present invention provides a method for the treatment of AFP-related diseases, including infusing the isolated T cell expressing the TCR of the present invention into a patient, and preferably, the T cell is derived from the patient himself. Generally, the method includes (1) isolating T cells from a patient, (2) in vitro transducing the T cells with the nucleic acid molecule of the present invention or a nucleic acid molecule capable of encoding TCR molecules of the present invention, and (3) infusing genetically engineered T cells into patients in vivo. The number of cells to be isolated, transfected and reinfused can be determined by a physician.

Main Advantages of the Present Invention (1) The TCR of the present invention can bind to the AFP antigen short peptide complex FMNKFIYEI-HLA A0201, and the cells transduced with the TCR of the present invention can be specifically activated.

The invention is further illustrated by the following specific examples. It is to be understood that these examples are for illustrative purposes only and are not intended to limit the scope of the invention. The experimental methods in the following examples which do not specify the specific conditions are usually performed under conventional conditions, for example, conditions described in Sambrook and Russell et al., Molecular Cloning—A Laboratory Manual (Third Edition) (2001) CSHL Publishing company, or in accordance with the conditions recommended by the manufacturer. Percentages and parts are by weight unless otherwise stated.

Example 1. Cloning of AFP Antigen Short Peptide Specific T Cells

The synthetic short peptide FMNKFIYEI (SEQ ID NO.: 9; Beijing Cypress Gene Technology Co., Ltd.) was used to stimulate peripheral blood lymphocytes (PBL) from healthy volunteers with genotype HLA-A0201. The FMNKFIYEI short peptide was refolded with biotin-labeled HLA-A0201 to prepare pHLA haploid. These haploids were combined with PE-labeled streptavidin (BD Company) to form PE-labeled tetramers, and the tetramers and anti-CD8-APC double-positive cells were sorted. The sorted cells were amplified and the secondary sorting was performed according to the above method, and then the limiting dilution method was performed for monoclone. Monoclonal cells were stained with tetramers, and the screened double positive clones are shown in FIG. 3. The screened double-positive clones are necessary to meet further functional tests.

The function and specificity of the T cell clone were further tested by ELISPOT experiment. A skilled person is familiar with the method of using ELISPOT assay to detect cell function. The effector cells used in the IFN-γELISPOT experiment of this example are the T cell clones obtained in the present invention, the target cells are T2 cells loaded with the short peptides of the present invention, and the control group are T2 cells loaded with other short peptides and T2 cells without any short peptide.

Figure 14:
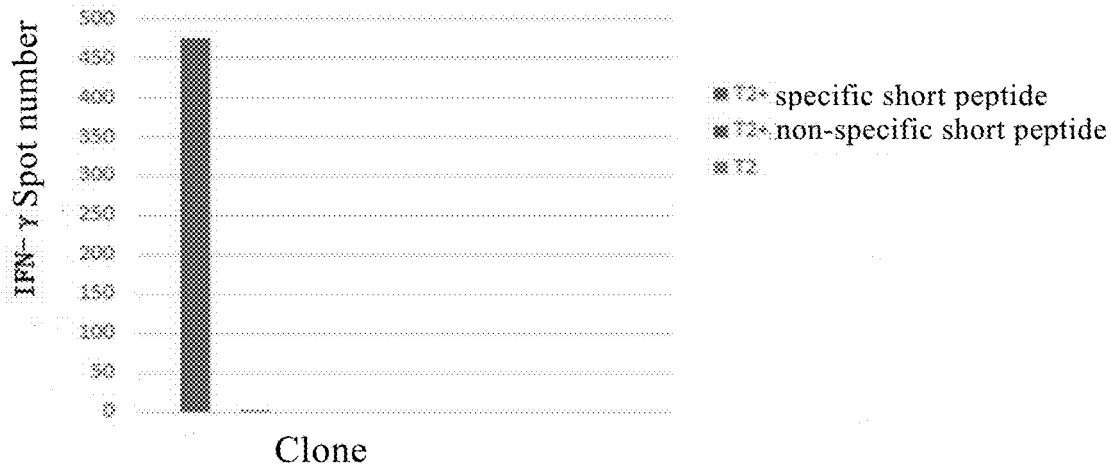
FIG. 14 shows the result of the ELISPOT activation function verification of the obtained T cell clone.

Firstly, a ELISPOT plate was prepared. The procedure of the ELISPOT experiment is as follows: the components to be tested were added to the ELISPOT plate in the following order: 40 µl T2 cells 5×10⁵ cells/ml (i.e., 20,000 T2 cells/well), 40 µl effector cells (2000 T cell clones/well), the experimental group was added with 20 µl of specific short peptide, the control group was added with 20 µl of non-specific short peptide, the blank group was added with 20 µl of medium (test medium), and duplicate wells were set. And then the plate was incubated overnight (37° C., 5% CO$_2$). Then the plate was washed and subjected to secondary detection and color development. The plate was dried for 1 hour, and then the spots formed on the membrane were counted with an immunospot plate reader (ELISPOT READER system; AID company). The experimental results are shown in FIG. 14. The obtained specific antigen-specific T cell clones have specific responses to T2 cells loaded with short peptides of the present invention, but basically no response to T2 cells loaded with other irrelevant peptides and T2 cells loaded not loaded with short peptides.

Example 2. Obtaining TCR Gene of T Cell Clone Specific for Short Peptide of AFP Antigen and Constructing Vector Quick-RNA™ MiniPrep (ZYMO research) was used to extract the total RNA of the antigen short peptide FMNK-FIYEI-specific and HLA-A0201-restricted T cell clones selected in Example 1. SMART RACE cDNA amplification kit (clontech) was used to synthesize the cDNA, and the used primers were designed in the C-terminal conserved region of the human TCR gene. The sequence was cloned into a T vector (TAKARA) for sequencing. It should be noted that this sequence is a complementary sequence and does not contain introns. After sequencing, the sequence structures of the α chain and β chain of the TCR expressed by the double-positive clone are shown in FIG. 1 and FIG. 2, respectively. FIG. 1a, FIG. 1b, FIG. 1c, FIG. 1d, FIG. 1e and FIG. 1f are the TCR α chain variable domain amino acid sequence, TCR α chain variable domain nucleotide sequence, TCR α chain amino acid sequence, TCR α chain nucleotide sequence, the TCR α chain amino acid sequence with a leader sequence and the TCR α chain nucleotide sequence with the leader sequence; and FIG. 2a, FIG. 2b, FIG. 2c, FIG. 2d, FIG. 2e and FIG. 2f are the TCR β chain variable domain amino acid sequence, TCR β chain variable domain nucleotide sequence, TCR β chain amino acid sequence, TCR β chain nucleotide sequence, the TCR β chain amino acid sequence with a leader sequence and the TCR β chain nucleotide sequence with the leader sequence.

It was identified that the α chain comprises CDRs with the following amino acid sequences:

α CDR1- DSAIYN (SEQ ID NO: 10)

α CDR2- IQSSQRE (SEQ ID NO: 11)

α CDR3- AVNSGGSNYKLT (SEQ ID NO: 12)

and the β chain comprises CDRs with the following amino acid sequences:

β CDR1- SGHVS (SEQ ID NO: 13)

β CDR2- FQNEAQ (SEQ ID NO: 14)

β CDR3- ASSLFGQGREKLF. (SEQ ID NO: 15)

The full-length genes of TCR α chain and β chain were cloned into lentiviral expression vector pLenti (addgene) by overlapping PCR. Specifically, the full-length genes of TCR α chain and TCR β chain were connected by overlap PCR to obtain TCRα-2A-TCRβ fragment. The lentiviral expression vector and TCRα-2A-TCRβ were digested and connected to obtain the pLenti-TRA-2A-TRB-IRES-NGFR plasmid. As a control, a lentiviral vector pLenti-eGFP expressing eGFP was also constructed. Then 293T/17 was used to package pseudovirus.

Example 3. Expression, Refolding and Purification of Soluble TCR Specific for AFP Antigen Short Peptide For obtaining a soluble TCR molecule, the α and β chains of the TCR molecule of the present invention may only contain the variable domain and part of the constant domain, respectively, and a cysteine residue was introduced into the constant domains of the α and β chains to form an artificial interchain disulfide bond. The positions for introducing cysteine residues were Thr48 of TRAC*01 exon 1 and Ser57 of TRBC1*01 or TRBC2*01 exon 1, respectively; the amino acid sequence and nucleotide sequence of the α chain were shown in FIG. 4a and FIG. 4b, respectively, and the amino acid sequence and nucleotide sequence of the β chain were shown in FIG. 5a and FIG. 5b, respectively. The target gene sequences of the above-mentioned TCR α and β chains were synthesized and inserted into an expression vector pET28a+ (Novagene) according to the method described in "Molecular Cloning a Laboratory Manual" (3$^{rd}$ version, Sambrook and Russell), the upstream and downstream cloning sites were NcoI and NotI respectively. The inserted fragment was confirmed by sequencing.

The expression vectors for TCR α and β chains were transformed into bacteria BL21 (DE3) by chemical transformation, and the bacteria were grown in LB medium, and induced with a final concentration of 0.5 mM IPTG at OD$_{600}$=0.6. After TCR α and β chains were expressed, the formed inclusion bodies were extracted with BugBuster Mix (Novagene) and repeatedly washed with BugBuster solution. The inclusion bodies were finally dissolved in 6 M guanidine hydrochloride, 10 mM dithiothreitol (DTT), 10 mM ethylenediamine acetic acid (EDTA), 20 mM Tris (pH 8.1).

The dissolved TCR α and β chains were quickly mixed in 5 M urea, 0.4 M arginine, 20 mM Tris (pH 8.1), 3.7 mM cystamine, 6.6 mM β-mercapoethylamine (4° C.) at amass ratio of 1:1, with a final concentration of 60 mg/mL. After mixing, the solution was subjected to dialysis against 10 times volume of deionized water (4° C.). After 12 hours, the deionized water was changed to a buffer (20 mM Tris, pH 8.0) and the dialysis was conducted at 4° C. for another 12 hours. After dialysis, the solution was filtered through a 0.45 µM filter membrane and purified through an anion exchange column (HiTrap Q HP, 5 ml, GE Healthcare). The eluted peak contained the successfully renatured α and β dimers of TCR, which was confirmed by SDS-PAGE. The TCR was then further purified through gel filtration chromatography (HiPrep 16/60, Sephacryl 5-100 HR, GE Healthcare). The purity of the purified TCR was determined by SDS-PAGE to be greater than 90%, and the concentration thereof was determined by the BCA method. The SDS-PAGE gel image of the soluble TCR obtained in the present invention is shown in FIG. 6.

Example 4. Generation of Soluble Single-Chain TCR Specific for AFP Antigen Short Peptide A method of site-directed mutagenesis was used according to WO2014/206304 to construct a stable single-chain TCR molecule consisting of TCR α and β chain variable domains of Example 2 connected by a flexible short peptide (linker). The amino acid sequence and nucleotide sequence of the single-chain TCR molecule are shown in FIGS. 7a and 7b, respectively. The amino acid sequence and nucleotide sequence of the α chain variable domain are shown in FIG. 8a and FIG. 8b respectively; the amino acid sequence and nucleotide sequence of the β chain variable domain are shown in FIG. 9a and FIG. 9b respectively; the amino acid sequence and nucleotide sequence of the linker are shown in FIG. 10a and FIG. 10b, respectively.

The target gene was digested with NcoI and NotI, and ligated with pET28a vector digested with NcoI and NotI. The ligation product was transformed into *E. coli* DH5α, plated on a kanamycin-containing LB plate, inverted and cultured at 37° C. overnight, and the positive clones were picked for PCR screening. Positive recombinants were sequenced to determine the correct sequence and the recombinant plasmid was extracted and transferred into *E. coli* BL21 (DE3) for expression.

Example 5. Expression, Refolding and Purification of Soluble Single-Chain TCR Specific for AFP Antigen Short Peptide All of BL21(DE 3) colonies containing the recombinant plasmid pET28a-template chain prepared in Example 4 were inoculated into LB medium containing kanamycin, and cultured at 37° C. until OD600 was 0.6-0.8. IPTG was added to a final concentration of 0.5 mM, and cultured at 37° C. for another 4 hrs. The cell pellets were harvested by centrifugation at 5000 rpm for 15 mins, and the cell pellets were lysed with Bugbuster Master Mix (Merck). The inclusion bodies were recovered by centrifugation at 6000 rpm for 15 min, followed by washing with Bugbuster (Merck) to remove cell debris and membrane fraction. The inclusion bodies were collected by centrifugation at 6000 rpm for 15 min, and dissolved in a buffer (20 mM Tris-HCl pH 8.0, 8 M urea), and the insoluble matters were removed by high-speed centrifugation. The supernatant was quantitatively determined by BCA method, and then dispensed and stored at −80° C. until use.

To 5 mg of dissolved single-chain TCR inclusion body protein, 2.5 mL of buffer (6 M Gua-HCl, 50 mM Tris-HCl pH 8.1, 100 mM NaCl, 10 mM EDTA) was added, then DTT was added to a final concentration of 10 mM, and incubated at 37° C. for 30 min. The single-chain TCRs as treated above was added dropwise to a 125 mL of refolding buffer (100 mM Tris-HCl pH 8.1, 0.4 M L-arginine, 5 M urea, 2 mM EDTA, 6.5 mM β-mercaptoethylamine, 1.87 mM Cystamine) with a syringe, and stirred at 4° C. for 10 min. Then the refolded solution was loaded into a cellulose membrane dialysis bag with a cut-off of 4 kDa, and the dialysis bag was placed in 1 L of pre-cooled water, and stirred slowly at 4° C. overnight. After 17 hours, the dialysis liquid was changed to 1 L of pre-chilled buffer (20 mM Tris-HCl pH 8.0) and dialysis was continued for 8 h at 4° C. The dialysis liquid was then replaced with the same fresh buffer and dialysis was continued overnight. After 17 hours, the sample was filtered through a 0.45 μm filter, vacuum degassed and purified through an anion exchange column (HiTrap Q HP, GE Healthcare) with a linear gradient elution of 0-1 M NaCl prepared with 20 mM Tris-HCl pH 8.0. The collected fractions were subjected to SDS-PAGE analysis, and the fractions containing single-chain TCRs were concentrated and further purified by a gel filtration column (Superdex 75 10/300, GE Healthcare), and the target components were also subjected to SDS-PAGE analysis.

The eluted fractions for BIAcore analysis was further tested for purity using gel filtration. The conditions were as follows: chromatographic column Agilent Bio SEC-3 (300 A, φ 7.8×300 mm), mobile phase 150 mM phosphate buffer, flow rate 0.5 mL/min, column temperature 25° C., and UV detection wavelength 214 nm.

Figure 11:
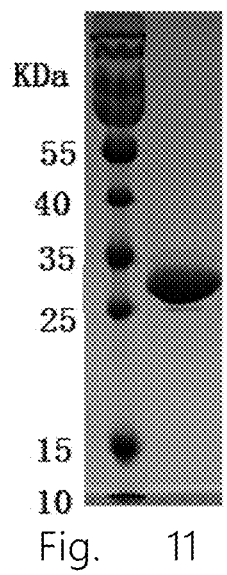
FIG. 11 is a gel image of soluble single-chain TCR obtained after purification. The left lane is the molecular weight marker, and the right lane is the non-reducing gel.

The SDS-PAGE gel image of the soluble single-chain TCR obtained in the present invention is shown in FIG. 11.

Example 6. Binding Characterization

BIAcore Analysis

This example proves that the soluble TCR molecule of the present invention can specifically bind to the FMNKFIYEI-HLA A0201 complex.

The binding activity of the TCR molecule obtained in Example 3 and Example 5 to FMNKFIYEI-HLA A0201 complex was detected using BIAcore T200 real-time analysis system. The anti-streptavidin antibody (GenScript) was added to a coupling buffer (10 mM sodium acetate buffer, pH 4.77), and then the antibody was passed through a CM5 chip pre-activated with EDC and NHS to immobilize the antibody on the surface of the chip. The unreacted activated surface was finally blocked with a solution of ethanolamine in hydrochloric acid to complete the coupling process at a coupling level of about 15,000 RU.

A low concentration of streptavidin flowed over the surface of the antibody-coated chip, then FMNKFIYEI-HLA A0201 complex flowed through the detection channel with another channel being used as a reference channel. 0.05 mM biotin flowed over the chip for 2 min at a flow rate of 10 μL/min, thereby blocking the remaining binding sites for streptavidin.

The preparation process for the above FMNKFIYEI-HLA A0201 complex is described as follows:

a. Purification 100 ml of *E. coli* liquid induced to express heavy or light chain was collected, and centrifuged at 8000 g for 10 min at 4° C., and the cells were washed once with 10 ml of PBS, and then vigorously shaken in 5 ml of BugBuster Master Mix Extraction Reagents (Merck) for resuspending the cells. The suspension was incubated for 20 min at room temperature, and then centrifuged at 6000 g for 15 min at 4° C. The supernatant was discarded to collect inclusion bodies.

The above inclusion bodies was resuspended in 5 ml BugBuster Master Mix and incubated vertically at room temperature for 5 min. 30 ml of 10 time-diluted BugBuster was added, mixed, and centrifuged at 6000 g for 15 min at 4° C. The supernatant was discarded, 30 ml of 10 time-diluted BugBuster was added to resuspend the inclusion body, mixed, and centrifuged twice at 6000 g at 4° C. for 15 min. 30 ml of 20 mM Tris-HCl pH 8.0 was added to resuspend the inclusion bodies, mixed, and centrifuged at 6000 g at 4° C. for 15 min. Finally, inclusion bodies were dissolved in 20 mM Tris-HCl 8M urea, and the purity of inclusion bodies was determined by SDS-PAGE and the concentration was measured by BCA kit.

b. Refolding

Synthesized short peptide FMNKFIYEI (Beijing Saibaisheng Gene Technology Co., Ltd.) were dissolved in DMSO to a concentration of 20 mg/ml. Inclusion bodies of light and heavy chains were solubilized in 8 M urea, 20 mM Tris pH 8.0, 10 mM DTT, and further denatured by adding 3 M guanidine hydrochloride, 10 mM sodium acetate, 10 mM EDTA before refolding. FMNKFIYEI peptide was added to a refolding buffer (0.4 M L-arginine, 100 mM Tris pH 8.3, 2 mM EDTA, 0.5 mM oxidized glutathione, 5 mM reduced glutathione, 0.2 mM PMSF, cooled to 4° C.) at 25 mg/L (final concentration). Then 20 mg/L of light chain and 90 mg/L of heavy chain (final concentration, heavy chain was added in three portions, 8 h/portion) were successively added, and refolded at 4° C. for at least 3 days to completion of refolding, and SDS-PAGE was used to confirm refolding.

c. Purification Upon Refolding

The refolding buffer was replaced with 10 volumes of 20 mM Tris pH 8.0 for dialysis, and the buffer was exchanged for at least two times to substantially reduce the ionic strength of the solution. After dialysis, the protein solution was filtered through a 0.45 μm cellulose acetate filter and loaded onto a HiTrap Q HP (GE, General Electric Company) anion exchange column (5 ml bed volume). The protein was eluted with a linear gradient of 0-400 mM NaCl prepared in 20 mM Tris pH 8.0 using Akta Purifier (GE), and the pMHC was eluted at approximately 250 mM NaCl. Peak fractions were collected and the purity thereof was detected by SDS-PAGE.

d. Biotinylation

Purified pMHC molecules were concentrated in a Millipore ultrafiltration tube, while the buffer was replaced with 20 mM Tris pH 8.0, and then biotinylation reagent 0.05 M Bicine pH 8.3, 10 mM ATP, 10 mM MgOAc, 50 μM D-Biotin, 100 μg/ml BirA enzyme (GST-BirA) was added. The resulting mixture was incubated at room temperature overnight, and SDS-PAGE was used to detect the completion of biotinylation.

e. Purification of Biotinylated Complex

The biotinylated and labeled pMHC molecules were concentrated to 1 ml in a Millipore ultrafiltration tube. The biotinylated pMHC was purified by gel filtration chromatography. 1 ml of concentrated biotinylated pMHC molecules was loaded on a HiPrep™ 16/60 S200 HR column (GE) pre-equilibrated with filtered PBS using an Akta Purifier (GE) and eluted with PBS at a flow rate of 1 ml/min. The biotinylated pMHC molecules were eluted as a single peak at about 55 ml. The protein-containing fractions were combined and concentrated in a Millipore ultrafiltration tube. The concentration of protein was determined by BCA method (Thermo), protease inhibitor cocktail (Roche) was added and the biotinylated pMHC molecules were dispensed and stored at −80° C.

Figure 12:
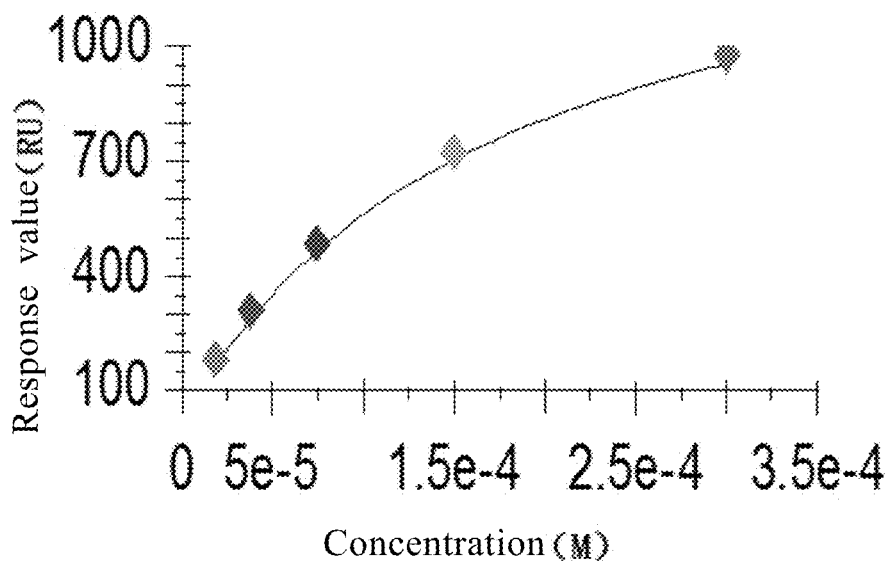
FIG. 12 is a BIAcore kinetic map of the binding of the soluble TCR of the present invention to FMNKFIYEI-HLA A0201 complex.
Figure 13:
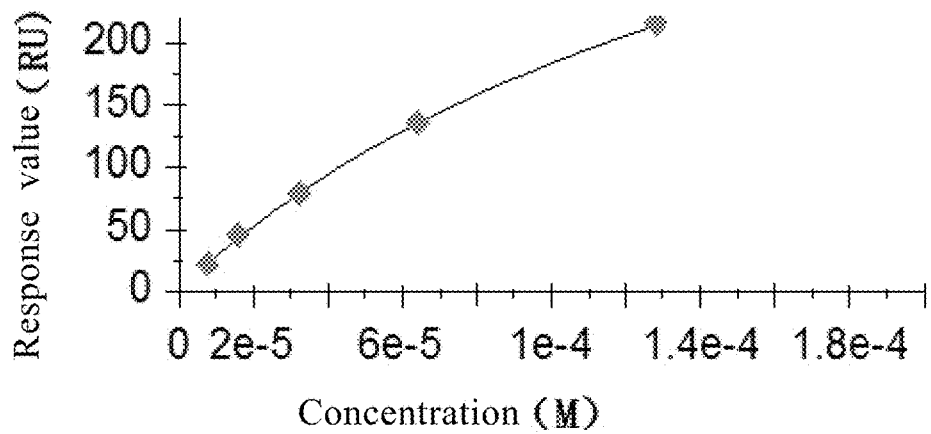
FIG. 13 is a BIAcore kinetic map of the binding of the soluble single-chain TCR of the present invention to FMNKFIYEI-HLA A0201 complex.

The kinetic patterns of the soluble TCR molecules of the present invention and the soluble single-chain TCR molecules constructed in the present invention binding to the FMNKFIYEI-HLA A0201 complex obtained by using BIAcore Evaluation software to calculate kinetic parameters are shown in FIG. 12 and FIG. 13, respectively. The pattern shows that both the soluble TCR molecules and soluble single-chain TCR molecules obtained in the present invention can bind to the FMNKFIYEI-HLA A0201 complex. The above method was also used to detect the binding activity of the soluble TCR molecule of the present invention to complexes of several other unrelated antigen short peptides with HLA, and the results showed that the TCR molecule of the present invention did not bind to other unrelated antigens.

Example 7. Activation Experiment of T Cell Transduced with TCR of the Present Invention A lentiviral vector containing the TCR target gene of the present invention was constructed, T cells were transduced, and an ELISPOT function verification assay was performed.

ELISPOT Protocol

The following experiments were performed to prove the specific activation response of T cells transduced by TCR of the present invention to target cells. The production of IFN-γ detected by ELISPOT assay was used as the readout value of T cell activation.

Reagents

Assay medium: 10% FBS (Gibco, Cat No., 16000-044), RPMI 1640 (Gibco, Cat No., C11875500bt)

Washing buffer (PBST): 0.01M PBS/0.05% Tween 20 PBS (Gibco, Cat No., C10010500BT)

PVDF ELISPOT 96 well-plate (Merck Millipore., Cat No., MSIPS4510)

Human IFN-γ ELISPOT PVDF-Enzyme Kit (BD) contains all the other necessary reagents (capture and detection antibody, streptavidin-alkaline phosphatase and BCIP/NBT solution)

Method

Preparation of Target Cells

The target cells used in this experiment were T2 cells loaded with specific short peptides. The target cells were prepared in the assay medium: the concentration of target cells wase adjusted to $2.0 \times 10^5$ cells/ml, and 100 microliters was added into each well to obtain $2.0 \times 10^4$ cells/well.

Preparation of Effector Cells

The effector cells (T cells) in this experiment were CD8$^+$ T cells transfected with TCR of the present invention specific to the AFP antigen short peptide, and CD8$^+$ T cells not transfected with the TCR of the present invention from the same volunteer were used as the control group. The T cells were stimulated with anti-CD3/CD28 coated beads (T cell amplification, life technologies), transduced with a lentivirus carrying the gene of TCR specific for AFP antigen short peptide, and expanded in 1640 medium containing 50 IU/ml of IL-2, 10 ng/ml of IL-7 and 10% FBS until 9-12 days after transduction. And then the cells were placed in the assay medium and washed by centrifugation at 300 g at room temperature for 10 minutes. The cells were then resuspended in the assay medium at 2× the desired final concentration. The negative control effector cells were treated in the same way.

Preparation of Solution of Short Peptide

The corresponding short peptide was added to the corresponding target cell (T2) assay group, so that the final concentration of the short peptide in the ELISPOT plate was 0.1 μg/ml, and then serially diluted. The control group was not diluted, and directly used in the assay at the highest concentration of the short peptide.

ELISPOT

According to the manufacturer's instructions, the plate was prepared as follows: the anti-human IFN-γ capture antibody was diluted at 1:200 with 10 ml of sterile PBS per plate, and then aliquots of 100 microliters of the diluted capture antibody were added to each well. The plate was incubated overnight at 4° C. After incubation, the plate was washed to remove excess of capture antibody. 100 μl/well of RPMI 1640 medium containing 10% FBS was added, and the plate was incubated at room temperature for 2 hours to block the plate. Then the medium was washed away from the plate, and any remaining wash buffer was removed by tapping the ELISPOT plate on a piece of paper.

Then the assay components were added to the ELISPOT plate in the following order:

100 microliters of target cells $2*10^5$ cells/ml (so as to get a total of about $2*10^4$ target cells/well).

100 microliters of effector cells ($1*10^4$ effector cells/well and AFP TCR positive T cell/well).

All wells were prepared in duplicate.

Then the plate was incubated overnight (37° C./5% $CO_2$). The next day, the medium was discarded, the plate was washed twice with double distilled water, then washed for three times with washing buffer, tapped on a piece of paper towel to remove residual washing buffer. Then the detection antibody was diluted at 1:200 with PBS containing 10% FBS, and added to each well at 100 μl/well. The plate was incubated at room temperature for 2 hours, then washed for 3 times with washing buffer, and tapped on a piece of paper towel to remove excess washing buffer.

Streptavidin-alkaline phosphatase was diluted at 1:100 with PBS containing 10% FBS, 100 microliters of diluted streptavidin-alkaline phosphatase was added to each well and the plate was incubated at room temperature for 1 hour. Then the plate was washed for 4 times with washing buffer, washed for 2 times with PBS, and tapped on a piece of paper towel to remove excess washing buffer and PBS. After washing, 100 μl/well of BCIP/NBT solution provided in the kit was added for development. During development, the plate was covered with a tin foil so as to keeping it in darkness, and let it stand for 5-15 minutes. During this period, the spots of the developing plate were routinely checked to determine the best time to quench the reaction. The BCIP/NBT solution was removed and the plate was rinsed with double distilled water to quench the development reaction, and spin-dried. Then the bottom of the well plate was removed, the plate was dried at room temperature until each well was completely dry. And then the immunospot plate counter (CTL, Cellular Technology Limited) was used to count the spots formed on the bottom membrane of the plate.

Results

The ELISPOT experiment (as described above) was used to test the release of IFN-γ from the T cells transduced with the TCR of the present invention in response to target cells loaded with AFP antigen short peptide FMNKFIYEI. Graphpad prism6 was used to plot the number of ELSPOT spots observed in each well.

Figure 15:
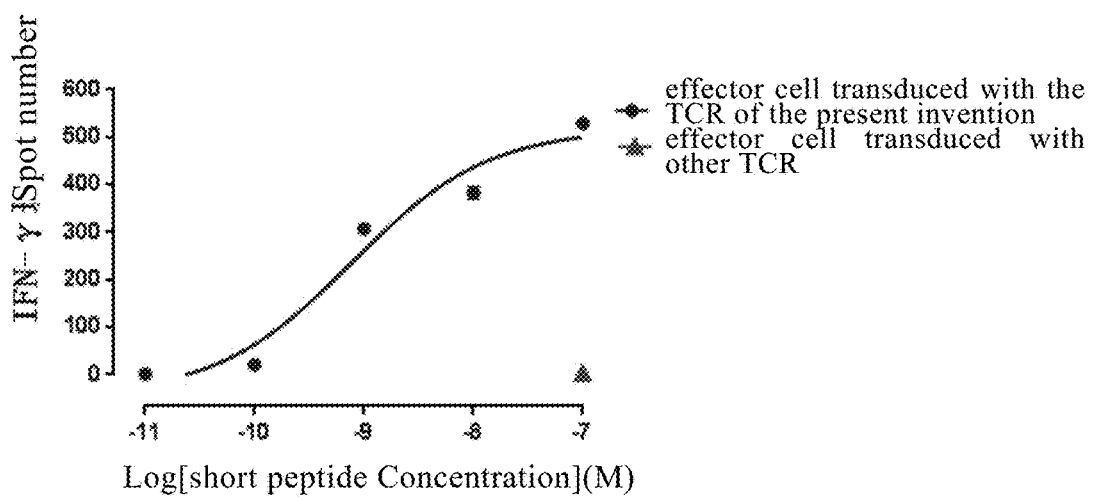
FIG. 15 shows the results of the ELISPOT activation function verification of the effector cells transduced with the TCR of the present invention.

The results of the experiment are shown in FIG. 15. The T cells (effector cells) transduced with the TCR of the present invention exhibit a good activation response to the target cells loaded with the specific short peptide, while the T cells (effector cells) transduced with other TCRs exhibit basically no activation response to the corresponding target cells.

All documents mentioned in the present application are hereby incorporated by reference in their entireties, as if each is incorporated by reference. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A T cell receptor (TCR) that binds to the FMNKFIYEI (SEQ ID NO: 9)-HLA A0201 complex; the TCR comprising a TCR α chain variable domain and a TCR β chain variable domain, wherein 3 complementary determining regions (CDR) of the TCR α chain variable domain are:
α CDR1-DSAIYN (SEQ ID NO: 10)
α CDR2-IQSSQRE (SEQ ID NO: 11)
α CDR3-AVNSGGSNYKLT (SEQ ID NO: 12); and/or
3 complementary determining regions of the TCR β chain variable domain are:
β CDR1-SGHVS (SEQ ID NO: 13)
β CDR2-FQNEAQ (SEQ ID NO: 14)
β CDR3-ASSLFGQGREKLF (SEQ ID NO: 15).

2. The TCR of claim 1, wherein the TCR comprises a TCR α chain variable domain and a TCR β chain variable domain, and the TCR α chain variable domain is an amino acid sequence having at least 90% sequence identity with SEQ ID NO: 1; and/or the TCR β chain variable domain is an amino acid sequence with at least 90% sequence identity with SEQ ID NO: 5.

3. The TCR of claim 1, wherein the TCR comprises a TCR α chain variable domain, the amino acid sequence of which is SEQ ID NO: 1.

4. The TCR of claim 1, wherein the TCR comprises a TCR β chain variable domain, the amino acid sequence of which is SEQ ID NO: 5.

5. The TCR of claim 1, wherein the TCR is a αβ heterodimer comprising a TCR α chain constant region TRAC*01 and a TCR β chain constant region TRBC1*01 or TRBC2*01.

6. The TCR of claim 5, wherein the amino acid sequence of the TCR α chain is SEQ ID NO: 3 and/or the amino acid sequence of the TCR β chain is SEQ ID NO: 7.

7. The TCR of claim 1, wherein the TCR is soluble.

8. The TCR of claim 7, wherein the TCR is a single-chain TCR; the TCR is formed by connecting the α chain variable domain and the β chain variable domain through a peptide linking sequence.

9. The TCR of claim 1, wherein the amino acid sequence of the α chain variable domain of the TCR comprises SEQ ID NO: 32 and/or the amino acid sequence of the β chain variable domain of the TCR comprises SEQ ID NO: 34.

10. The TCR of claim 9, wherein the amino acid sequence of the TCR is SEQ ID NO: 30.

11. The TCR of claim 7, wherein the TCR comprises (a) all or part of the TCR α chain except for its transmembrane domain, and (b) all or part of the TCR β chain except for its transmembrane domain;
and each of (a) and (b) comprise the functional variable domain, or the functional variable domain and at least a portion of the constant domain of the TCR chain, respectively.

12. The TCR of claim 11, wherein cysteine residues form an artificial disulfide bond between the α and β chain constant domains of the TCR; wherein the cysteine residues forming the artificial interchain disulfide bond in the TCR are substituted for one or more groups of amino acids selected from the following:
Thr48 of TRAC*01 exon 1 and Ser57 of TRBC1*01 or TRBC2*01 exon 1;
Thr45 of TRAC*01 exon 1 and Ser77 of TRBC1*01 or TRBC2*01 exon 1;
Tyr10 of TRAC*01 exon 1 and Ser17 of TRBC1*01 or TRBC2*01 exon 1;
Thr45 of TRAC*01 exon 1 and Asp59 of TRBC1*01 or TRBC2*01 exon 1;

Ser15 of TRAC*01 exon 1 and Glu15 of TRBC1*01 or TRBC2*01 exon 1;
Arg53 of TRAC*01 exon 1 and Ser54 of TRBC1*01 or TRBC2*01 exon 1;
Pro89 of TRAC*01 exon 1 and Ala19 of TRBC1*01 or TRBC2*01 exon 1; and
Tyr10 of TRAC*01 exon 1 and Glu20 of TRBC1*01 or TRBC2*01 exon 1.

13. The TCR of claim 12, wherein the amino acid sequence of the TCR α chain is SEQ ID NO: 26 and/or the amino acid sequence of the TCR β chain is SEQ ID NO: 28.

14. The TCR of claim 11, wherein an artificial interchain disulfide bond is contained between α chain variable region and β chain constant region of the TCR; cysteine residues forming the artificial interchain disulfide bond in the TCR are substituted for one or more groups of amino acids selected from the following:
amino acid at position 46 of TRAV and amino acid at position 60 of TRBC1*01 or TRBC2*01 exon 1;
amino acid at position 47 of TRAV and amino acid at position 61 of TRBC1*01 or TRBC2*01 exon 1;
amino acid at position 46 of TRAV and amino acid at position 61 of TRBC1*01 or TRBC2*01 exon 1; or
amino acid at position 47 of TRAV and amino acid at position 60 of TRBC1*01 or TRBC2*01 exon 1.

15. The TCR of claim 14, wherein the TCR comprises α chain variable domain and β chain variable domain as well as all or part of β chain constant domains except for its transmembrane domain, however it does not comprise α chain constant domain, and α chain variable domain and β chain of the TCR form a heterodimer.

16. The TCR of claim 1, wherein a conjugate binds to the α chain and/or β chain of the TCR at C- or N-terminal; the conjugate is a detectable label or a therapeutic agent; and more preferably, the therapeutic agent is an anti-CD3 antibody.

17. A multivalent TCR complex, wherein the multivalent TCR complex comprises at least two TCR molecules, and at least one TCR molecule is the TCR of claim 1.

18. A nucleic acid molecule, comprising a nucleic acid sequence encoding the TCR molecule of claim 1, or a complement sequence thereof.

19. The nucleic acid molecule of claim 18, wherein the nucleic acid molecule comprises the nucleotide sequence SEQ ID NO: 2 or SEQ ID NO: 33 encoding the variable domain of the TCR α chain.

20. The nucleic acid molecule of claim 18, wherein the nucleic acid molecule comprises the nucleotide sequence SEQ ID NO: 6 or SEQ ID NO: 35 encoding the variable domain of the TCR β chain.

21. The nucleic acid molecule of claim 18, wherein the nucleic acid molecule comprises the nucleotide sequence SEQ ID NO: 4 encoding the TCR α chain and/or the nucleotide sequence SEQ ID NO: 8 encoding the variable domain of the TCR β chain.

22. A vector, comprising the nucleic acid molecule of claim 18; preferably, the vector is a viral vector; and more preferably, the vector is a lentiviral vector.

23. An isolated host cell, having an exogenous nucleic acid molecule integrated into its genome or comprising a vector comprising the nucleic acid molecule;
wherein the nucleic acid molecule comprises a nucleic acid sequence encoding the TCR molecule of claim 1, or a complement sequence thereof.

24. A cell, wherein the cell is transduced with a nucleic acid molecule or a vector comprising the nucleic acid molecule; and preferably, the cell is a T cell or stem cell; wherein the nucleic acid molecule comprises a nucleic acid sequence encoding the TCR molecule of claim 1, or a complement sequence thereof.

25. A pharmaceutical composition, comprising a pharmaceutically acceptable carrier, and a TCR of claim 1, a multivalent TCR complex, or a cell; wherein the multivalent TCR complex comprises at least two TCR molecules, and at least one TCR molecule is the TCR of claim 1;
and the cell is transduced with a nucleic acid molecule or a vector comprising the nucleic acid molecule, and the nucleic acid molecule comprises a nucleic acid sequence encoding the TCR of claim 1, or a complement sequence thereof; and preferably, the cell is a T cell or stem cell.

26. A method for treating a disease, comprising administering an appropriate amount of a TCR of claim 1, a multivalent TCR complex, a cell, or a pharmaceutical composition to a subject in need thereof;
wherein the multivalent TCR complex comprises at least two TCR molecules, and at least one TCR molecule is the TCR of claim 1;
the cell is transduced with a nucleic acid molecule or a vector comprising the nucleic acid molecule, and the nucleic acid molecule comprises a nucleic acid sequence encoding the TCR of claim 1, or a complement sequence thereof; and preferably, the cell is a T cell or stem cell;
and the pharmaceutical composition comprises a pharmaceutically acceptable carrier, and the TCR of claim 1, the multivalent TCR complex or the cell
preferably, the tumor is a AFP antigen positive tumor; and more preferably, the tumor is hepatocellular carcinoma.

* * * * *

SEQUENCE LISTING

<160> NUMBER OF SEQ ID NOS: 37

<210> SEQ ID NO 1
<211> LENGTH: 114
<212> TYPE: PRT
<213> ORGANISM: Artificial Sequence
<220> FEATURE:
<223> OTHER INFORMATION: synthesized polypeptide

<400> SEQUENCE: 1

```
Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asn Ser Gly Gly
                85                  90                  95

Ser Asn Tyr Lys Leu Thr Phe Gly Lys Gly Thr Leu Leu Thr Val Asn
                100                 105                 110

Pro Asn
```

```
<210> SEQ ID NO 2
<211> LENGTH: 342
<212> TYPE: DNA
<213> ORGANISM: Artificial Sequence
<220> FEATURE:
<223> OTHER INFORMATION: synthesized polynucleotide

<400> SEQUENCE: 2
aaacaggagg tgacacagat tcctgcagct ctgagtgtcc cagaaggaga aaacttggtt      60
ctcaactgca gtttcactga tagcgctatt tacaacctcc agtggtttag gcaggaccct     120
gggaaaggtc tcacatctct gttgcttatt cagtcaagtc agagagagca acaagtgga     180 agacttaatg cctcgctgga taaatcatca ggacgtagta ctttatacat tgcagcttct     240
cagcctggtg actcagccac ctacctctgt gctgtgaata gtggaggtag caactataaa     300
ctgacatttg gaaaggaac tctcttaacc gtgaatccaa at                         342

<210> SEQ ID NO 3
<211> LENGTH: 254
<212> TYPE: PRT
<213> ORGANISM: Artificial Sequence
<220> FEATURE:
<223> OTHER INFORMATION: synthesized polypeptide

<400> SEQUENCE: 3
```

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Asn Ser Gly Gly
                85                  90                  95

Ser Asn Tyr Lys Leu Thr Phe Gly Lys Gly Thr Leu Leu Thr Val Asn
            100                 105                 110

Pro Asn Ile Gln Asn Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
    130                 135                 140

Thr Asn Val Ser Gln Ser Lys Asp Ser Asp Val Tyr Ile Thr Asp Lys
145                 150                 155                 160

Thr Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser Cys
        195                 200                 205

Asp Val Lys Leu Val Glu Lys Ser Phe Glu Thr Asp Thr Asn Leu Asn
    210                 215                 220

Phe Gln Asn Leu Ser Val Ile Gly Phe Arg Ile Leu Leu Leu Lys Val
225                 230                 235                 240

Ala Gly Phe Asn Leu Leu Met Thr Leu Arg Leu Trp Ser Ser
                245                 250

<210> SEQ ID NO 4
<211> LENGTH: 762
<212> TYPE: DNA
<213> ORGANISM: Artificial Sequence
<220> FEATURE:
<223> OTHER INFORMATION: synthesized polynucleotide

<400> SEQUENCE: 4

```
aaacaggagg tgacacagat tcctgcagct ctgagtgtcc cagaaggaga aaacttggtt      60
ctcaactgca gtttcactga tagcgctatt tacaacctcc agtggtttag gcaggaccct     120
gggaaaggtc tcacatctct gttgcttatt cagtcaagtc agagagagca aacaagtgga     180
agacttaatg cctcgctgga taaatcatca ggacgtagta ctttatacat tgcagcttct     240
cagcctggtg actcagccac ctacctctgt gctgtgaata gtggaggtag caactataaa     300
ctgacatttg gaaaggaac tctcttaacc gtgaatccaa atatccagaa ccctgaccct     360
gccgtgtacc agctgagaga ctctaaatcc agtgacaagt ctgtctgcct attcaccgat     420
tttgattctc aaacaaatgt gtcacaaagt aaggattctg atgtgtatat cacagacaaa     480
actgtgctag acatgaggtc tatggacttc aagagcaaca gtgctgtggc ctggagcaac     540
aaatctgact ttgcatgtgc aaacgccttc aacaacagca ttattccaga agacaccttc     600
ttccccagcc cagaaagttc ctgtgatgtc aagctggtcg agaaaagctt tgaaacagat     660
acgaacctaa actttcaaaa cctgtcagtg attgggttcc gaatcctcct cctgaaagtg     720
gccgggttta atctgctcat gacgctgcgg ctgtggtcca gc                        762
```

<210> SEQ ID NO 5
<211> LENGTH: 115
<212> TYPE: PRT
<213> ORGANISM: Artificial Sequence
<220> FEATURE:
<223> OTHER INFORMATION: synthesized polypeptide

<400> SEQUENCE: 5

```
Gly Ala Gly Val Ser Gln Ser Pro Arg Tyr Lys Val Ala Lys Arg Gly
1               5                   10                  15

Gln Asp Val Ala Leu Arg Cys Asp Pro Ile Ser Gly His Val Ser Leu
            20                  25                  30

Phe Trp Tyr Gln Gln Ala Leu Gly Gln Gly Pro Glu Phe Leu Thr Tyr
        35                  40                  45

Phe Gln Asn Glu Ala Gln Leu Asp Lys Ser Gly Leu Pro Ser Asp Arg
    50                  55                  60

Phe Phe Ala Glu Arg Pro Glu Gly Ser Val Ser Thr Leu Lys Ile Gln
65                  70                  75                  80

Arg Thr Gln Gln Glu Asp Ser Ala Val Tyr Leu Cys Ala Ser Ser Leu
                85                  90                  95

Phe Gly Gln Gly Arg Glu Lys Leu Phe Phe Gly Ser Gly Thr Gln Leu
            100                 105                 110

Ser Val Leu
        115
```

<210> SEQ ID NO 6
<211> LENGTH: 345
<212> TYPE: DNA
<213> ORGANISM: Artificial Sequence
<220> FEATURE:
<223> OTHER INFORMATION: synthesized polynucleotide

<400> SEQUENCE: 6

```
ggtgctggag tctcccagtc ccctaggtac aaagtcgcaa agagaggaca ggatgtagct    60
ctcaggtgtg atccaatttc gggtcatgta tccctttttt ggtaccaaca ggccctgggg   120
caggggccag agtttctgac ttatttccag aatgaagctc aactagacaa atcggggctg   180
cccagtgatc gcttctttgc agaaaggcct gagggatccg tctccactct gaagatccag   240
cgcacacagc aggaggactc cgccgtgtat ctctgtgcca gcagcttatt cgggcaggga   300
cgggaaaaac tgttttttgg cagtggaacc cagctctctg tcttg                   345
```

<210> SEQ ID NO 7
<211> LENGTH: 292
<212> TYPE: PRT
<213> ORGANISM: Artificial Sequence
<220> FEATURE:
<223> OTHER INFORMATION: synthesized polypeptide

<400> SEQUENCE: 7

```
Gly Ala Gly Val Ser Gln Ser Pro Arg Tyr Lys Val Ala Lys Arg Gly
1               5                   10                  15

Gln Asp Val Ala Leu Arg Cys Asp Pro Ile Ser Gly His Val Ser Leu
            20                  25                  30

Phe Trp Tyr Gln Gln Ala Leu Gly Gln Gly Pro Glu Phe Leu Thr Tyr
        35                  40                  45

Phe Gln Asn Glu Ala Gln Leu Asp Lys Ser Gly Leu Pro Ser Asp Arg
    50                  55                  60

Phe Phe Ala Glu Arg Pro Glu Gly Ser Val Ser Thr Leu Lys Ile Gln
65                  70                  75                  80

Arg Thr Gln Gln Glu Asp Ser Ala Val Tyr Leu Cys Ala Ser Ser Leu
                85                  90                  95

Phe Gly Gln Gly Arg Glu Lys Leu Phe Phe Gly Ser Gly Thr Gln Leu
            100                 105                 110

Ser Val Leu Glu Asp Leu Asn Lys Val Phe Pro Pro Glu Val Ala Val
        115                 120                 125

Phe Glu Pro Ser Glu Ala Glu Ile Ser His Thr Gln Lys Ala Thr Leu
    130                 135                 140

Val Cys Leu Ala Thr Gly Phe Phe Pro Asp His Val Glu Leu Ser Trp
145                 150                 155                 160

Trp Val Asn Gly Lys Glu Val His Ser Gly Val Ser Thr Asp Pro Gln
                165                 170                 175

Pro Leu Lys Glu Gln Pro Ala Leu Asn Asp Ser Arg Tyr Cys Leu Ser
            180                 185                 190

Ser Arg Leu Arg Val Ser Ala Thr Phe Trp Gln Asn Pro Arg Asn His
        195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp Cys Gly Phe Thr Ser Val Ser Tyr Gln Gln Gly
                245                 250                 255

Val Leu Ser Ala Thr Ile Leu Tyr Glu Ile Leu Leu Gly Lys Ala Thr
            260                 265                 270

Leu Tyr Ala Val Leu Val Ser Ala Leu Val Leu Met Ala Met Val Lys
        275                 280                 285

Arg Lys Asp Phe
    290
```

<210> SEQ ID NO 8
<211> LENGTH: 876
<212> TYPE: DNA
<213> ORGANISM: Artificial Sequence
<220> FEATURE:
<223> OTHER INFORMATION: synthesized polynucleotide

<400> SEQUENCE: 8

```
ggtgctggag tctcccagtc ccctaggtac aaagtcgcaa agagaggaca ggatgtagct      60
ctcaggtgtg atccaatttc gggtcatgta tccctttttt ggtaccaaca ggccctgggg     120
caggggccag agtttctgac ttatttccag aatgaagctc aactagacaa atcggggctg     180
cccagtgatc gcttctttgc agaaaggcct gagggatccg tctccactct gaagatccag     240
cgcacacagc aggaggactc cgccgtgtat ctctgtgcca gcagcttatt cgggcaggga     300
cgggaaaaac tgttttttgg cagtggaacc cagctctctg tcttggagga cctgaacaag     360
gtgttcccac ccgaggtcgc tgtgtttgag ccatcagaag cagagatctc cacacccaa      420 aaggccacac tggtgtgcct ggccacaggc ttcttcccg accacgtgga gctgagctgg     480
tgggtgaatg gaaggaggt gcacagtggg gtcagcacgg accgcagcc cctcaaggag       540 cagcccgccc tcaatgactc agatactgc ctgagcagcc gcctgagggt ctcggccacc      600
ttctggcaga accccgcaa ccacttccgc tgtcaagtcc agttctacgg gctctcggag      660
aatgacgagt ggacccagga tagggccaaa cccgtcaccc agatcgtcag cgccgaggcc     720 tgggtagag cagactgtgg ctttacctcg gtgtcctacc agcaaggggt cctgtctgcc      780
accatcctct atgagatcct gctagggaag gccaccctgt atgctgtgct ggtcagcgcc     840
cttgtgttga tggccatggt caagagaaag gatttc                              876
```

<210> SEQ ID NO 9
<211> LENGTH: 9
<212> TYPE: PRT
<213> ORGANISM: Artificial Sequence
<220> FEATURE:
<223> OTHER INFORMATION: synthesized polypeptide

<400> SEQUENCE: 9

Phe Met Asn Lys Phe Ile Tyr Glu Ile
1               5

<210> SEQ ID NO 10
<211> LENGTH: 6
<212> TYPE: PRT
<213> ORGANISM: Artificial Sequence
<220> FEATURE:
<223> OTHER INFORMATION: synthesized polypeptide

<400> SEQUENCE: 10

Asp Ser Ala Ile Tyr Asn
1               5

<210> SEQ ID NO 11
<211> LENGTH: 7
<212> TYPE: PRT
<213> ORGANISM: Artificial Sequence
<220> FEATURE:
<223> OTHER INFORMATION: synthesized polypeptide

<400> SEQUENCE: 11

Ile Gln Ser Ser Gln Arg Glu
1               5

<210> SEQ ID NO 12
<211> LENGTH: 12
<212> TYPE: PRT
<213> ORGANISM: Artificial Sequence
<220> FEATURE:
<223> OTHER INFORMATION: synthesized polypeptide

<400> SEQUENCE: 12

Ala Val Asn Ser Gly Gly Ser Asn Tyr Lys Leu Thr
1               5                   10

<210> SEQ ID NO 13
<211> LENGTH: 5
<212> TYPE: PRT
<213> ORGANISM: Artificial Sequence
<220> FEATURE:
<223> OTHER INFORMATION: synthesized polypeptide

<400> SEQUENCE: 13

Ser Gly His Val Ser
1               5

<210> SEQ ID NO 14
<211> LENGTH: 6
<212> TYPE: PRT
<213> ORGANISM: Artificial Sequence
<220> FEATURE:
<223> OTHER INFORMATION: synthesized polypeptide

<400> SEQUENCE: 14

Phe Gln Asn Glu Ala Gln
1               5

<210> SEQ ID NO 15
<211> LENGTH: 13
<212> TYPE: PRT
<213> ORGANISM: Artificial Sequence
<220> FEATURE:
<223> OTHER INFORMATION: synthesized polypeptide

<400> SEQUENCE: 15

Ala Ser Ser Leu Phe Gly Gln Gly Arg Glu Lys Leu Phe
1               5                   10

<210> SEQ ID NO 16
<211> LENGTH: 18
<212> TYPE: DNA
<213> ORGANISM: Artificial Sequence
<220> FEATURE:
<223> OTHER INFORMATION: synthesized polynucleotide

<400> SEQUENCE: 16
gatagcgcta tttacaac                                                 18

<210> SEQ ID NO 17
<211> LENGTH: 21
<212> TYPE: DNA
<213> ORGANISM: Artificial Sequence
<220> FEATURE:
<223> OTHER INFORMATION: synthesized polynucleotide

<400> SEQUENCE: 17
attcagtcaa gtcagagaga g                                             21

<210> SEQ ID NO 18

<210> SEQ ID NO 18
<211> LENGTH: 36
<212> TYPE: DNA
<213> ORGANISM: Artificial Sequence
<220> FEATURE:
<223> OTHER INFORMATION: synthesized polynucleotide

<400> SEQUENCE: 18
gctgtgaata gtggaggtag caactataaa ctgaca                36

<210> SEQ ID NO 19
<211> LENGTH: 15
<212> TYPE: DNA
<213> ORGANISM: Artificial Sequence
<220> FEATURE:
<223> OTHER INFORMATION: synthesized polynucleotide

<400> SEQUENCE: 19
tcgggtcatg tatcc                                        15

<210> SEQ ID NO 20
<211> LENGTH: 18
<212> TYPE: DNA
<213> ORGANISM: Artificial Sequence
<220> FEATURE:
<223> OTHER INFORMATION: synthesized polynucleotide

<400> SEQUENCE: 20
ttccagaatg aagctcaa                                     18

<210> SEQ ID NO 21
<211> LENGTH: 39
<212> TYPE: DNA
<213> ORGANISM: Artificial Sequence
<220> FEATURE:
<223> OTHER INFORMATION: synthesized polynucleotide

<400> SEQUENCE: 21
gccagcagct tattcgggca gggacgggaa aaactgttt              39

<210> SEQ ID NO 22
<211> LENGTH: 273
<212> TYPE: PRT
<213> ORGANISM: Artificial Sequence
<220> FEATURE:
<223> OTHER INFORMATION: synthesized polypeptide

<400> SEQUENCE: 22

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Asn
            100                 105                 110

Ser Gly Gly Ser Asn Tyr Lys Leu Thr Phe Gly Lys Gly Thr Leu Leu
        115                 120                 125

```
Thr Val Asn Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser
```

<210> SEQ ID NO 23
<211> LENGTH: 819
<212> TYPE: DNA
<213> ORGANISM: Artificial Sequence
<220> FEATURE:
<223> OTHER INFORMATION: synthesized polynucleotide

<400> SEQUENCE: 23

```
atggagaccc tcttgggcct gcttatcctt tggctgcagc tgcaatgggt gagcagcaaa      60
caggaggtga cacagattcc tgcagctctg agtgtcccag aaggagaaaa cttggttctc     120
aactgcagtt tcactgatag cgctatttac aacctccagt ggtttaggca ggaccctggg     180
aaaggtctca catctctgtt gcttattcag tcaagtcaga gagagcaaac aagtggaaga     240
cttaatgcct cgctggataa atcatcagga cgtagtactt tatacattgc agcttctcag     300
cctggtgact cagccaccta cctctgtgct gtgaatagtg gaggtagcaa ctataaactg     360
acatttggaa aggaactctc ttaaccgtga atccaaata  tccagaaccc tgaccctgcc     420
gtgtaccagc tgagagactc taaatccagt gacaagtctg tctgcctatt caccgatttt     480
gattctcaaa caaatgtgtc acaaagtaag gattctgatg tgtatatcac agacaaaact     540
gtgctagaca tgaggtctat ggacttcaag agcaacagtg ctgtggcctg agcaacaaa     600
tctgactttg catgtgcaaa cgccttcaac aacagcatta ttccagaaga cacctcttc     660
cccagcccag aaagttcctg tgatgtcaag ctggtcgaga aagctttga aacagatacg     720
aacctaaact tcaaaacct gtcagtgatt gggttccgaa tcctcctcct gaaagtggcc     780
gggtttaatc tgctcatgac gctgcggctg tggtccagc                            819
```

<210> SEQ ID NO 24
<211> LENGTH: 311
<212> TYPE: PRT
<213> ORGANISM: Artificial Sequence
<220> FEATURE:
<223> OTHER INFORMATION: synthesized polypeptide

<400> SEQUENCE: 24

Met Gly Thr Arg Leu Leu Cys Trp Val Val Leu Gly Phe Leu Gly Thr

```
              1               5                  10                 15
Asp His Thr Gly Ala Gly Val Ser Gln Ser Pro Arg Tyr Lys Val Ala
            20                  25                 30
Lys Arg Gly Gln Asp Val Ala Leu Arg Cys Asp Pro Ile Ser Gly His
            35                  40                 45
Val Ser Leu Phe Trp Tyr Gln Gln Ala Leu Gly Gln Gly Pro Glu Phe
            50                  55                 60
Leu Thr Tyr Phe Gln Asn Glu Ala Gln Leu Asp Lys Ser Gly Leu Pro
65                  70                  75                 80
Ser Asp Arg Phe Phe Ala Glu Arg Pro Glu Gly Ser Val Ser Thr Leu
                    85                  90                 95
Lys Ile Gln Arg Thr Gln Gln Glu Asp Ser Ala Val Tyr Leu Cys Ala
                    100                 105                110
Ser Ser Leu Phe Gly Gln Gly Arg Glu Lys Leu Phe Gly Ser Gly
                    115                 120                125
Thr Gln Leu Ser Val Leu Glu Asp Leu Asn Lys Val Phe Pro Pro Glu
            130                 135                140
Val Ala Val Phe Glu Pro Ser Glu Ala Glu Ile Ser His Thr Gln Lys
145                 150                 155                160
Ala Thr Leu Val Cys Leu Ala Thr Gly Phe Phe Pro Asp His Val Glu
                    165                 170                175
Leu Ser Trp Trp Val Asn Gly Lys Glu Val His Ser Gly Val Ser Thr
                    180                 185                190
Asp Pro Gln Pro Leu Lys Glu Gln Pro Ala Leu Asn Asp Ser Arg Tyr
                    195                 200                205
Cys Leu Ser Ser Arg Leu Arg Val Ser Ala Thr Phe Trp Gln Asn Pro
            210                 215                220
Arg Asn His Phe Arg Cys Gln Val Gln Phe Tyr Gly Leu Ser Glu Asn
225                 230                 235                240
Asp Glu Trp Thr Gln Asp Arg Ala Lys Pro Val Thr Gln Ile Val Ser
                    245                 250                255
Ala Glu Ala Trp Gly Arg Ala Asp Cys Gly Phe Thr Ser Val Ser Tyr
                    260                 265                270
Gln Gln Gly Val Leu Ser Ala Thr Ile Leu Tyr Glu Ile Leu Leu Gly
                    275                 280                285
Lys Ala Thr Leu Tyr Ala Val Leu Val Ser Ala Leu Val Leu Met Ala
            290                 295                300
Met Val Lys Arg Lys Asp Phe
305                 310

<210> SEQ ID NO 25
<211> LENGTH: 933
<212> TYPE: DNA
<213> ORGANISM: Artificial Sequence
<220> FEATURE:
<223> OTHER INFORMATION: synthesized polynucleotide

<400> SEQUENCE: 25
atgggcacca ggctcctctg ctgggtggtc ctgggtttcc tagggacaga tcacacaggt      60
gctggagtct cccagtcccc taggtacaaa gtcgcaaaga gaggacagga tgtagctctc     120
aggtgtgatc caatttcggg tcatgtatcc ctttttttggt accaacaggc cctggggcag    180
gggccagagt tctgactta tttccagaat gaagctcaac tagacaaatc ggggctgccc      240
agtgatcgct tctttgcaga aaggcctgag ggatccgtct ccactctgaa gatccagcgc     300
```

```
acacagcagg aggactccgc cgtgtatctc tgtgccagca gcttattcgg gcagggacgg    360
gaaaaactgt tttttggcag tggaacccag ctctctgtct tggaggacct gaacaaggtg    420
ttcccacccg aggtcgctgt gtttgagcca tcagaagcag agatctccca cacccaaaag    480
gccacactgg tgtgcctggc cacaggcttc ttccccgacc acgtggagct gagctggtgg    540
gtgaatggga aggaggtgca cagtggggtc agcacggacc cgcagcccct caaggagcag    600
cccgccctca tgactccaga atactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaaccc gtcacccaga tcgtcagcgc cgaggcctgg    780
ggtagagcag actgtggctt tacctcggtg tcctaccagc aaggggtcct gtctgccacc    840
atcctctatg agatcctgct agggaaggcc accctgtatg ctgtgctggt cagcgccctt    900
gtgttgatgg ccatggtcaa gagaaaggat ttc                                 933
```

```
<210> SEQ ID NO 26
<211> LENGTH: 208
<212> TYPE: PRT
<213> ORGANISM: Artificial Sequence
<220> FEATURE:
<223> OTHER INFORMATION: synthesized polypeptide

<400> SEQUENCE: 26
```

Met Lys Gln Glu Val Thr Gln Ile Pro Ala Ala Leu Ser Val Pro Glu
1               5                   10                  15

Gly Glu Asn Leu Val Leu Asn Cys Ser Phe Thr Asp Ser Ala Ile Tyr
            20                  25                  30

Asn Leu Gln Trp Phe Arg Gln Asp Pro Gly Lys Gly Leu Thr Ser Leu
        35                  40                  45

Leu Leu Ile Gln Ser Ser Gln Arg Glu Gln Thr Ser Gly Arg Leu Asn
    50                  55                  60

Ala Ser Leu Asp Lys Ser Ser Gly Arg Ser Thr Leu Tyr Ile Ala Ala
65                  70                  75                  80

Ser Gln Pro Gly Asp Ser Ala Thr Tyr Leu Cys Ala Val Asn Ser Gly
                85                  90                  95

Gly Ser Asn Tyr Lys Leu Thr Phe Gly Lys Gly Thr Leu Leu Thr Val
            100                 105                 110

Asn Pro Asn Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

```
<210> SEQ ID NO 27
<211> LENGTH: 624
<212> TYPE: DNA
<213> ORGANISM: Artificial Sequence
<220> FEATURE:
<223> OTHER INFORMATION: synthesized polynucleotide
```

<400> SEQUENCE: 27

```
atgaaacagg aagtgaccca gattcctgca gctctgagtg tcccagaagg agaaaacttg      60
gttctcaact gcagtttcac tgatagcgct atttacaacc tccagtggtt taggcaggac     120
cctgggaaag gtctcacatc tctgttgctt attcagtcaa gtcagagaga gcaaacaagt     180
ggaagactta atgcctcgct ggataaatca tcaggacgta gtactttata cattgcagct     240
tctcagcctg gtgactcagc cacctacctc tgtgctgtga atagtggagg tagcaactat     300
aaactgacat ttggaaaagg aactctctta accgtgaatc caaatatcca gaaccctgac     360
cctgccgtgt accagctgag agactctaag tcgagtgaca agtctgtctg cctattcacc     420
gattttgatt ctcaaacaaa tgtgtcacaa agtaaggatt ctgatgtgta tatcacagac     480
aaatgtgtgc tagacatgag gtctatggac ttcaagagca cagtgctgt ggcctggagc      540
aacaaatctg actttgcatg tgcaaacgcc ttcaacaaca gcattattcc agaagacacc     600
ttcttcccca gcccagaaag ttcc                                            624
```

<210> SEQ ID NO 28
<211> LENGTH: 246
<212> TYPE: PRT
<213> ORGANISM: Artificial Sequence
<220> FEATURE:
<223> OTHER INFORMATION: synthesized polypeptide

<400> SEQUENCE: 28

```
Met Gly Ala Gly Val Ser Gln Ser Pro Arg Tyr Lys Val Ala Lys Arg
1               5                   10                  15

Gly Gln Asp Val Ala Leu Arg Cys Asp Pro Ile Ser Gly His Val Ser
            20                  25                  30

Leu Phe Trp Tyr Gln Gln Ala Leu Gly Gln Gly Pro Glu Phe Leu Thr
        35                  40                  45

Tyr Phe Gln Asn Glu Ala Gln Leu Asp Lys Ser Gly Leu Pro Ser Asp
    50                  55                  60

Arg Phe Phe Ala Glu Arg Pro Glu Gly Ser Val Ser Thr Leu Lys Ile
65                  70                  75                  80

Gln Arg Thr Gln Gln Glu Asp Ser Ala Val Tyr Leu Cys Ala Ser Ser
                85                  90                  95

Leu Phe Gly Gln Gly Arg Glu Lys Leu Phe Phe Gly Ser Gly Thr Gln
            100                 105                 110

Leu Ser Val Leu Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Cys Thr Asp Pro
                165                 170                 175

Gln Pro Leu Lys Glu Gln Pro Ala Leu Asn Asp Ser Arg Tyr Ala Leu
            180                 185                 190

Ser Ser Arg Leu Arg Val Ser Ala Thr Phe Trp Gln Asp Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240
```

Ala Trp Gly Arg Ala Asp
                245

<210> SEQ ID NO 29
<211> LENGTH: 738
<212> TYPE: DNA
<213> ORGANISM: Artificial Sequence
<220> FEATURE:
<223> OTHER INFORMATION: synthesized polynucleotide

<400> SEQUENCE: 29

| | | | | | | |
|---|---|---|---|---|---|---|
| atgggtgcag | gtgttagcca | gtcccctagg | tacaaagtcg | caaagagagg | acaggatgta | 60 |
| gctctcaggt | gtgatccaat | tcgggtcat | gtatcccttt | tttggtacca | acaggccctg | 120 |
| gggcaggggc | cagagtttct | gacttatttc | agaatgaag | ctcaactaga | caaatcgggg | 180 |
| ctgcccagtg | atcgcttctt | tgcagaaagg | cctgagggat | ccgtctccac | tctgaagatc | 240 |
| cagcgcacac | agcaggagga | ctccgccgtg | tatctctgtg | ccagcagctt | attcgggcag | 300 |
| ggacgggaaa | aactgttttt | tggcagtgga | acccagctct | ctgtcttgga | ggacctgaaa | 360 |
| aacgtgttcc | cacccgaggt | cgctgtgttt | gagccatcag | aagcagagat | ctcccacacc | 420 |
| caaaaggcca | cactggtgtg | cctggccacc | ggtttctacc | ccgaccacgt | ggagctgagc | 480 |
| tggtgggtga | atgggaagga | ggtgcacagt | ggggtctgca | cagacccgca | gcccctcaag | 540 |
| gagcagcccg | ccctcaatga | ctccagatac | gctctgagca | gccgcctgag | ggtctcggcc | 600 |
| accttctggc | aggaccccc g | caaccacttc | cgctgtcaag | tccagttcta | cgggctctcg | 660 |
| gagaatgacg | agtggaccca | ggatagggcc | aaacccgtca | cccagatcgt | cagcgccgag | 720 |
| gcctggggta | gagcagac | | | | | 738 |

<210> SEQ ID NO 30
<211> LENGTH: 253
<212> TYPE: PRT
<213> ORGANISM: Artificial Sequence
<220> FEATURE:
<223> OTHER INFORMATION: synthesized polypeptide

<400> SEQUENCE: 30

Ala Lys Gln Glu Val Thr Gln Ser Pro Ala Ser Leu Ser Val Pro Glu
1               5                   10                  15

Gly Glu Asn Val Ser Ile Asn Cys Ser Phe Thr Asp Ser Ala Ile Tyr
            20                  25                  30

Asn Leu Gln Trp Phe Arg Gln Asp Pro Gly Lys Gly Leu Thr Ser Leu
        35                  40                  45

Leu Leu Ile Gln Ser Ser Gln Arg Glu Gln Thr Ser Gly Arg Leu Asn
    50                  55                  60

Ala Ser Leu Asp Lys Ser Ser Gly Arg Ser Thr Leu Tyr Ile Glu Asp
65                  70                  75                  80

Val Gln Pro Gly Asp Ser Ala Thr Tyr Leu Cys Ala Val Asn Ser Gly
                85                  90                  95

Gly Ser Asn Tyr Lys Leu Thr Phe Gly Lys Gly Thr Lys Leu Thr Val
            100                 105                 110

Asn Pro Gly Gly Gly Ser Glu Gly Gly Gly Ser Glu Gly Gly Gly Ser
        115                 120                 125

Glu Gly Gly Gly Ser Glu Gly Gly Thr Gly Gly Ala Gly Val Ser Gln
    130                 135                 140

Ser Pro Arg Tyr Leu Ser Val Lys Arg Gly Gln Asp Val Thr Leu Arg
145                 150                 155                 160

Cys Asp Pro Ile Ser Gly His Val Ser Leu Phe Trp Tyr Gln Gln Ala
                165                 170                 175

Pro Gly Gln Gly Pro Glu Phe Leu Thr Tyr Phe Gln Asn Glu Ala Gln
            180                 185                 190

Leu Asp Lys Ser Gly Leu Pro Ser Asp Arg Phe Phe Ala Glu Arg Pro
        195                 200                 205

Glu Gly Ser Val Ser Thr Leu Lys Ile Gln Arg Val Gln Pro Glu Asp
    210                 215                 220

Ser Ala Val Tyr Leu Cys Ala Ser Ser Leu Phe Gly Gln Gly Arg Glu
225                 230                 235                 240

Lys Leu Phe Phe Gly Ser Gly Thr Gln Leu Ser Val Asp
                245                 250

<210> SEQ ID NO 31
<211> LENGTH: 759
<212> TYPE: DNA
<213> ORGANISM: Artificial Sequence
<220> FEATURE:
<223> OTHER INFORMATION: synthesized polynucleotide

<400> SEQUENCE: 31
gctaaacaag aagttactca aagcccggcg agcctgagcg tgccggaggg tgaaaacgtt      60
agcatcaact gcagcttcac cgacagcgcg atttacaacc tgcaatggtt tcgtcaggac     120
ccgggcaagg gcctgaccag cctgctgctg atccagagca gcaacgtgag cagaccagc     180 ggtcgtctga cgcgagcct ggacaaaagc agcggccgta gcaccctgta tattgaagac     240
gtgcaaccgg tgatagcgc gacctacctg tgcgcggtta acagcggtgg cagcaactat     300
aagctgacct ttggcaaggg caccaaactg accgttaacc cgggtggcgg tagcgagggc     360
ggtggcagcg aaggtggcgg tagcgagggc ggtggcagcg aaggtggcac cggtggcgcg     420
ggtgtgagcc aaagcccgcg ttacctgagc gtgaaacgtg gtcaggacgt taccctgcgt     480
tgcgatccga tcagcggcca cgttagcctg ttctggtatc agcaagcgcc gggtcagggt     540
ccggagttcc tgacctattt tcaaaacgaa gcgcagctgg acaagagcgg tctgccgagc     600
gatcgtttct tgcggagcg tccggaaggc agcgtgagca ccctgaaaat tcaacgtgtg     660
cagccggagg acagcgcggt ttatctgtgc gcgagcagcc tgtttggtca aggccgtgaa     720
aaactgttct tggtagcgg cacccagctg agcgttgat                            759

<210> SEQ ID NO 32
<211> LENGTH: 114
<212> TYPE: PRT
<213> ORGANISM: Artificial Sequence
<220> FEATURE:
<223> OTHER INFORMATION: synthesized polypeptide

<400> SEQUENCE: 32

Ala Lys Gln Glu Val Thr Gln Ser Pro Ala Ser Leu Ser Val Pro Glu
1               5                   10                  15

Gly Glu Asn Val Ser Ile Asn Cys Ser Phe Thr Asp Ser Ala Ile Tyr
            20                  25                  30

Asn Leu Gln Trp Phe Arg Gln Asp Pro Gly Lys Gly Leu Thr Ser Leu
        35                  40                  45

Leu Leu Ile Gln Ser Ser Gln Arg Glu Gln Thr Ser Gly Arg Leu Asn
    50                  55                  60

Ala Ser Leu Asp Lys Ser Ser Gly Arg Ser Thr Leu Tyr Ile Glu Asp
65                  70                  75                  80

Val Gln Pro Gly Asp Ser Ala Thr Tyr Leu Cys Ala Val Asn Ser Gly
                85                  90                  95

Gly Ser Asn Tyr Lys Leu Thr Phe Gly Lys Gly Thr Lys Leu Thr Val
            100                 105                 110

Asn Pro

<210> SEQ ID NO 33
<211> LENGTH: 342
<212> TYPE: DNA
<213> ORGANISM: Artificial Sequence
<220> FEATURE:
<223> OTHER INFORMATION: synthesized polynucleotide

<400> SEQUENCE: 33
gctaaacaag aagttactca aagcccggcg agcctgagcg tgccggaggg tgaaaacgtt      60
agcatcaact gcagcttcac cgacagcgcg atttacaacc tgcaatggtt tcgtcaggac     120
ccgggcaagg gcctgaccag cctgctgctg atccagagca gccaacgtga gcagaccagc     180
ggtcgtctga acgcgagcct ggacaaaagc agcggccgta gcaccctgta tattgaagac     240
gtgcaaccgg tgatagcgc gacctacctg tgcgcggtta acagcggtgg cagcaactat     300
aagctgacct ttggcaaggg caccaaactg accgttaacc cg                       342

<210> SEQ ID NO 34
<211> LENGTH: 114
<212> TYPE: PRT
<213> ORGANISM: Artificial Sequence
<220> FEATURE:
<223> OTHER INFORMATION: synthesized polypeptide

<400> SEQUENCE: 34

Ala Gly Val Ser Gln Ser Pro Arg Tyr Leu Ser Val Lys Arg Gly Gln
1               5                   10                  15

Asp Val Thr Leu Arg Cys Asp Pro Ile Ser Gly His Val Ser Leu Phe
            20                  25                  30

Trp Tyr Gln Gln Ala Pro Gly Gln Gly Pro Glu Phe Leu Thr Tyr Phe
        35                  40                  45

Gln Asn Glu Ala Gln Leu Asp Lys Ser Gly Leu Pro Ser Asp Arg Phe
    50                  55                  60

Phe Ala Glu Arg Pro Glu Gly Ser Val Ser Thr Leu Lys Ile Gln Arg
65                  70                  75                  80

Val Gln Pro Glu Asp Ser Ala Val Tyr Leu Cys Ala Ser Ser Leu Phe
                85                  90                  95

Gly Gln Gly Arg Glu Lys Leu Phe Phe Gly Ser Gly Thr Gln Leu Ser
            100                 105                 110

Val Asp

<210> SEQ ID NO 35
<211> LENGTH: 342
<212> TYPE: DNA
<213> ORGANISM: Artificial Sequence
<220> FEATURE:
<223> OTHER INFORMATION: synthesized polynucleotide

<400> SEQUENCE: 35
gcgggtgtga gccaaagccc gcgttacctg agcgtgaaac gtggtcagga cgttaccctg      60
cgttgcgatc cgatcagcgg ccacgttagc ctgttctggt atcagcaagc gccgggtcag     120
ggtccggagt tcctgaccta ttttcaaaac gaagcgcagc tggacaagag cggtctgccg     180

```
agcgatcgtt tctttgcgga gcgtccggaa ggcagcgtga gcaccctgaa aattcaacgt      240
gtgcagccgg aggacagcgc ggtttatctg tgcgcgagca gcctgtttgg tcaaggccgt      300
gaaaaactgt tctttggtag cggcacccag ctgagcgttg at                         342
```

```
<210> SEQ ID NO 36
<211> LENGTH: 25
<212> TYPE: PRT
<213> ORGANISM: Artificial Sequence
<220> FEATURE:
<223> OTHER INFORMATION: synthesized polypeptide

<400> SEQUENCE: 36

Gly Gly Gly Ser Glu Gly Gly Ser Glu Gly Gly Gly Ser Glu Gly
1               5                   10                  15

Gly Gly Ser Glu Gly Gly Thr Gly Gly
            20                  25

<210> SEQ ID NO 37
<211> LENGTH: 75
<212> TYPE: DNA
<213> ORGANISM: Artificial Sequence
<220> FEATURE:
<223> OTHER INFORMATION: synthesized polynucleotide

<400> SEQUENCE: 37
ggtggcggta gcgagggcgg tggcagcgaa ggtggcggta gcgagggcgg tggcagcgaa       60
ggtggcaccg gtggc                                                       75
```